United States Patent [19]

Misra et al.

[11] Patent Number: 5,290,799

[45] Date of Patent: * Mar. 1, 1994

[54] 7-OXABICYCLOHEPTYL SUBSTITUTED HETEROCYCLIC THIOAMIDE PROSTAGLANDIN ANALOGS USEFUL IN THE TREATMENT OF THROMBOTIC AND VASOSPASTIC DISEASE

[75] Inventors: Raj N. Misra, Hopewell; Philip M. Sher, Plainsboro; Philip D. Stein, Princeton; Steven E. Hall, Trenton; David Floyd, Pennington, all of N.J.; Joel C. Barrish, Holland, Pa.

[73] Assignee: E. R. Squibb & Sons, Inc., Princeton, N.J.

[*] Notice: The portion of the term of this patent subsequent to Mar. 31, 2009 has been disclaimed.

[21] Appl. No.: 584,969

[22] Filed: Sep. 19, 1990

[51] Int. Cl.$^5$ ............... C07D 403/04; C07D 413/04; C07D 417/04; A61K 31/425

[52] U.S. Cl. .................... 514/365; 514/374; 514/397; 548/200; 548/236; 548/311.4

[58] Field of Search ................ 548/200, 236, 311.4; 514/365, 374, 397

[56] References Cited

U.S. PATENT DOCUMENTS

| | | | |
|---|---|---|---|
| 4,654,355 | 3/1987 | Nakane | 514/382 |
| 4,663,336 | 5/1987 | Nakane | 514/382 |
| 4,738,978 | 4/1988 | Nakane | 514/382 |
| 4,837,234 | 6/1989 | Jones | 514/469 |
| 5,100,889 | 3/1992 | Misra | 514/365 |

FOREIGN PATENT DOCUMENTS 374952 6/1990 European Pat. Off. .

OTHER PUBLICATIONS

AS Belo Bioorg Chem, 4, Mar. 1981-SU278256 (23, Nov. 1987) CO7c-177 CO7d-261/06.

Chem. Abs. SA Selects: Prostaglandins Issue 12, 1988, 108:198903m. Kuz'mitskii, B. B. et al.

CA Selects: Prostaglandins, Issue 12, 1988, 108:204363d, Lakhvich, F. A. et al.

Primary Examiner—Robert Gerstl
Attorney, Agent, or Firm—Burton Rodney

[57] ABSTRACT

7-Oxabicycloheptane substituted prostaglandin analogs useful in treating thrombotic and vasospastic disease have the structural formula

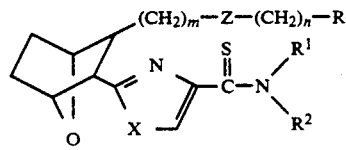

wherein m is 1, 2 or 3; n is 1, 2, 3 or 4; Z is —(CH$_2$)$_2$—, —CH=CH— or

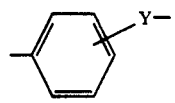

wherein Y is O, a single bond or vinyl, with the proviso that when n is O, if Z is

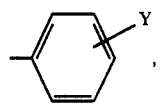

then Y cannot be O, and when Z is —CH=CH—, n is 1, 2, 3 or 4; and when Y=vinyl, n=0; R is CO$_2$H, CO$_2$-lower alkyl, CH$_2$OH, CO$_2$alkali metal, CONHSOR$^3$, CONHR$^{3a}$ or —CH$_2$-5-tetrazolyl, X is O, S or NH; and where R$^1$, R$^2$, R$^3$ and R$^{3a}$ are as defined herein.

25 Claims, No Drawings

7-OXABICYCLOHEPTYL SUBSTITUTED HETEROCYCLIC THIOAMIDE PROSTAGLANDIN ANALOGS USEFUL IN THE TREATMENT OF THROMBOTIC AND VASOSPASTIC DISEASE

DESCRIPTION OF THE INVENTION

The present invention relates to 7-oxabicycloheptyl substituted heterocyclic thioamide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic disease, and have good duration of action. These compounds have the structural formula I

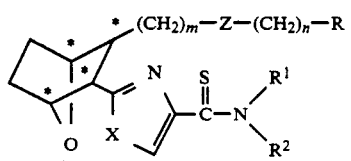

and including all stereoisomers thereof, wherein
m is 1, 2 or 3; n is 0, 1, 2, 3 or 4;
Z is —$(CH_2)_2$—, —CH=CH— or

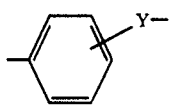

wherein Y is O, a single bond or vinyl (—CH=CH—), with the provisos that when n is 0, if Z is

then Y cannot be O; and when Z is —CH=CH—, n is 1,2,3, or 4; and when Y=vinyl, n=0;
R is $CO_2H$, $CO_2$lower alkyl, $CO_2$alkali metal, $CH_2OH$, $CONHSO_2R^3$, $CONHR^{3a}$, or

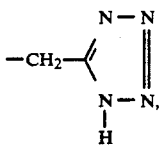

(—$CH_2$-5-tetrazolyl);
X is O, S or NH;
$R^1$ is hydrogen, lower alkyl, lower alkenyl, lower alkynyl, aralkyl, aryl, cycloalkyl, cycloalkylalkyl, cycloheteroalkyl, cycloheteroalkylalkyl, heteroaryl or heteroarylalkyl, each of $R^1$ being unsubstituted or optionally substituted with a lower alkyl, aryl, cycloalkyl, or cycloalkylalkyl group;
$R^2$ is hydrogen, lower alkyl, aryl, or aralkyl; or
$R^1$ and $R^2$ together with the nitrogen to which they are linked may form a 5- to 8-membered ring;
$R^3$ is lower alkyl, aryl or aralkyl; and
$R^{3a}$ is hydrogen, lower alkyl, aryl or aralkyl.

Thus, the compounds of the invention include the following types of compounds:

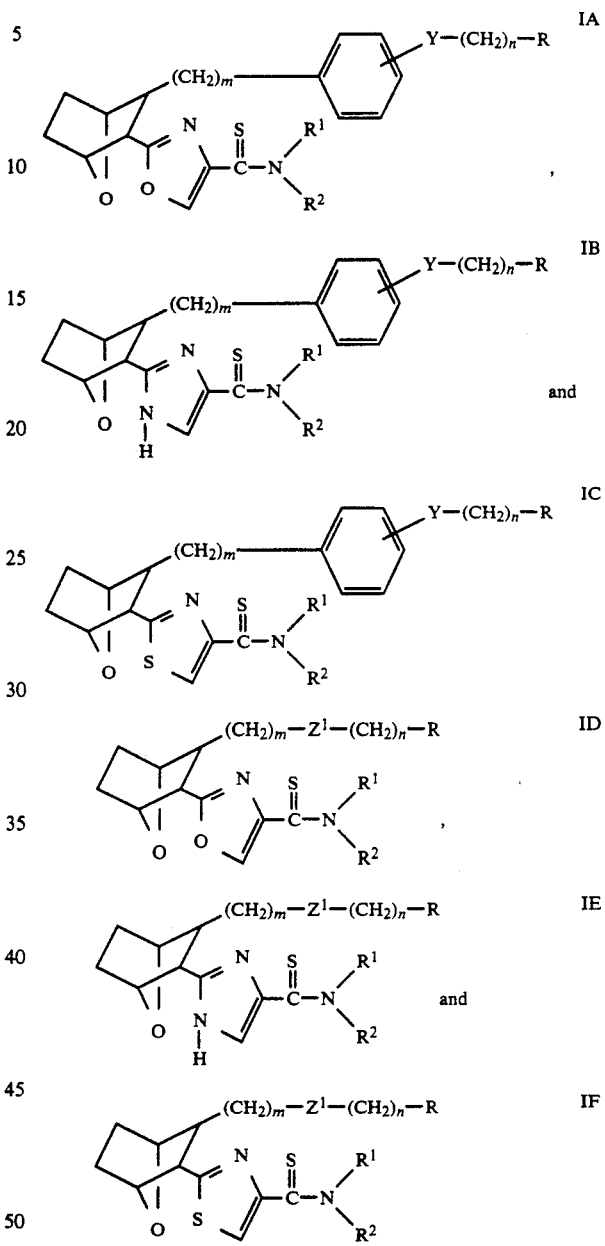

wherein in formulae ID, IE and IF, $Z^1$ is —CH=CH— or —$(CH_2)_2$—.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent, an alkylcycloalkyl substituent, hydroxy or a carboxy substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The term "aryl" or "Ar" as employed herein refers to monocyclic or bicyclic aromatic groups containing from 6 to 10 carbons in the ring portion, such as phenyl, naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "lower alkenyl" or "alkenyl" as employed herein with respect to the $R^1$ substituent includes a carbon chain of up to 16 carbons, preferably 3 to 10 carbons, containing one double bond which will be separated from "N" by at least one saturated carbon moiety such as —(CH$_2$)$_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein with respect to the $R^1$ substituent includes a carbon chain of up to 16 carbons, bond which will be separated from "N" by at least one saturated carbon moiety such as —(CH$_2$)$_{q'}$— where q' can be 1 to 14, such as 2-propynyl, 2-butynyl, 3-butynyl and the like.

The term "cycloheteroalkyl" as used herein as an $R^1$ substituent refers to a 5-, 6- or 7-membered saturated ring which includes 1 or 2 hetero atoms such as nitrogen, oxygen and/or sulfur, and which is linked to the "N" of the

group through a carbon atom either beta or gamma to a heteroatom, such as

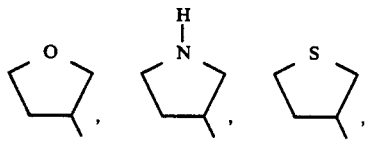

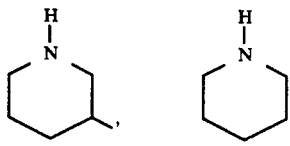

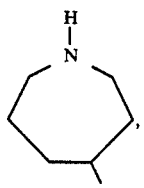
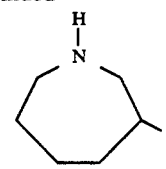

and the like.

The term "heteroaryl" or heteroaromatic as an $R^1$ substituent refers to a 5- or 6-membered aromatic ring which includes 1 or 2 hetero atoms such as nitrogen, oxygen or sulfur, which are not directly linked through a hetero atom to the "N" of the

group, such as

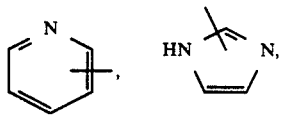

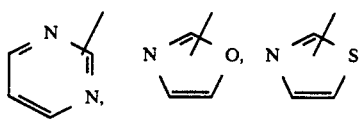

and the like.

The term "cycloheteroalkylalkyl" as defined by $R^1$ refers to 5-, 6- or 7-membered saturated ring which includes 1 or 2 heteroatoms such as nitrogen, oxygen or sulfur, and is linked to the "N" of the

group through a (CH$_2$)$_x$ chain wherein x is 1 to 12, preferably 1 to 8, such as

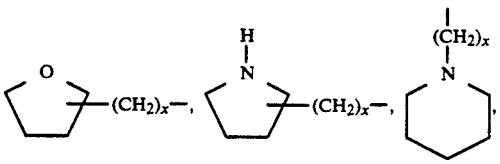

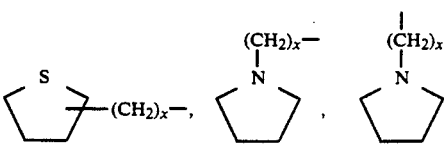

-continued

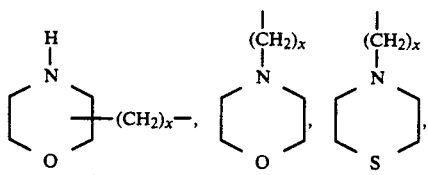

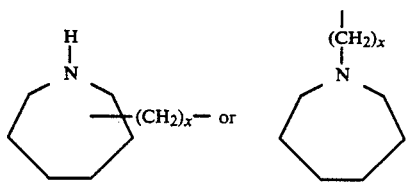

The term "heteroarylalkyl" as defined by $R^1$ refers to a 5- 6- or 7-membered aromatic ring which includes 1, 2, 3 or 4 heteroatoms such as nitrogen, oxygen or sulfur, and is linked to the "N" of the

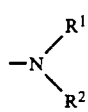

group through a —$(CH_2)_{x'}$— chain where x' is 1 to 12, preferably 1 to 8, such as

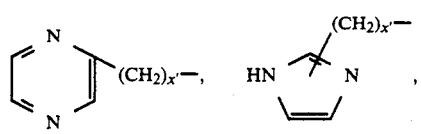

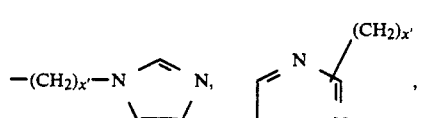

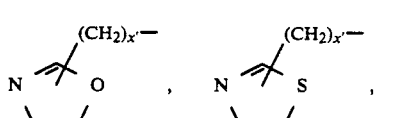

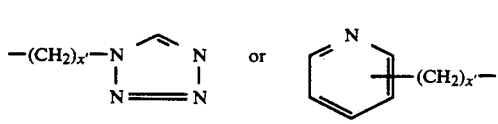

Preferred are those compounds of formula I wherein Z is

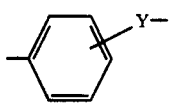

and X is O. More preferred are compound of formula I wherein Z— is

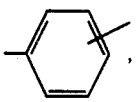

m is 1, n is 1 or 2, Y is a single bond, X is O, R is $CO_2H$, $R^1$ is substituted alkyl or a cycloheteroalkylalkyl and $R^2$ is H or lower alkyl, and —Y—$(CH_2)_n$—R is in the ortho or meta position.

Also preferred are compounds of formula I wherein Z is —CH=CH— in the cis configuration, m is 1, n is 2 or 3, R is $CO_2H$, $R^1$ is substituted phenylalkyl or cyclohexylalkyl and $R^2$ is H or methyl.

The compounds of formula I of the invention may be prepared as follows.

The various compounds of the invention wherein Z is

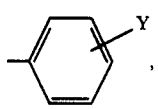

may be prepared as outlined below.

Compounds of the invention where Y is a single bond, n is 1, 2, 3 or 4 and X is O are prepared starting with bromophenylalkyl alcohol A

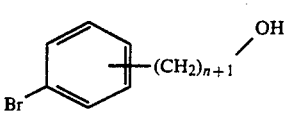

wherein n is 1, 2, 3 or 4 which is treated with a protecting compound such as t-butylchlorodiphenylsilane, in the presence of an amine base such as triethylamine and an inert solvent, employing conventional procedures, to form the protected bromophenylalkyl compound B

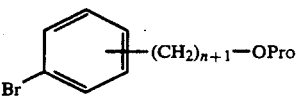

wherein Pro represents a protecting group.

Examples of protecting compounds suitable for use herein in reacting with bromophenalkyl alcohol A include but are not limited to

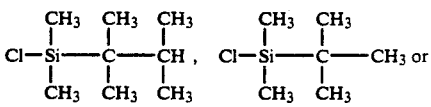

(chlorodimethylthexylsilane (chlorodimethyl-t-butylsilane)

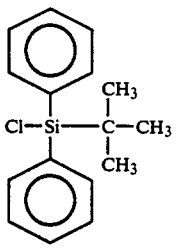

(t-butylchlorodiphenylsilane)

The protected compound B is then transmetallated by treatment with t-$C_4H_9Li$ or n-$C_4H_9Li$ in the presence of diethyl ether or tetrahydrofuran at reduced temperature of from about $-100°$ to about $0°$ C. or is preferably subjected to a Grignard reaction by treatment with magnesium in the presence of an inert organic solvent such as tetrahydrofuran (THF) or diethyl ether and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

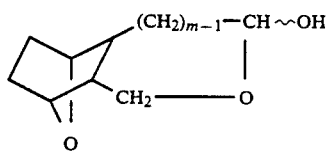

employing a molar ratio of C:B of within the range of from about 1:2 to about 1:4, in the presence of an inert organic solvent such as THF at a reduced temperature of from about $-78°$ to about $25°$ C., to form the condensed 7-oxabicycloheptane compound II

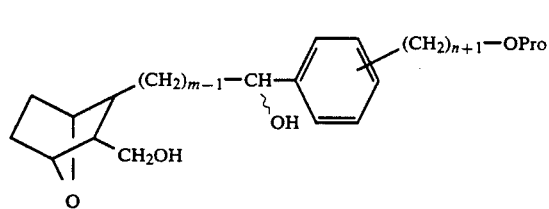

The condensed compound II is then subjected to hydrogenolysis by treatment with hydrogen in the presence of a catalyst such as palladium hydroxide on charcoal in acetic acid or an inert organic solvent such as ethyl acetate, to form the alcohol III

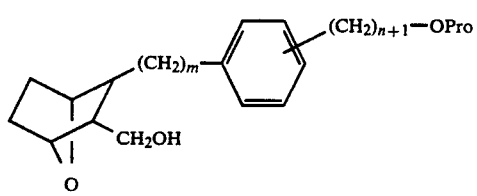

When the protecting group (Pro) in III is thexyldimethylsilyl or t-butyldimethylsilyl, alcohol III may be subjected to acetylation by treatment with acetyl chloride in the presence of pyridine and methylene chloride to acetylate the free alcohol and the so-formed acetate is deprotected by conventional procedures, for example, by treatment with aqueous hydrofluoric acid in the presence of acetonitrile to cleave off the silyl protecting group to form IIIA

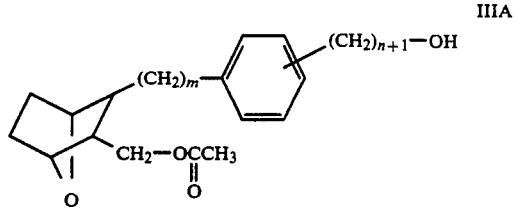

IIIA is then treated with a protecting compound such as t-butyldiphenylsilyl chloride in the presence of a catalyst such as 4,4-dimethylaminopyridine and an amine such as triethylamine and methylene chloride to add the protecting group and then the acetate is removed by treatment with aqueous hydroxide in tetrahydrofuran or excess methyllithium in the presence of an inert solvent such as diethyl ether to form IIIB

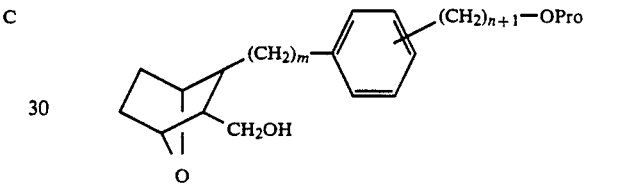

(where Pro is t-butyldiphenylsilyl)

The protected alcohol IIIB is then subjected to a Jones oxidation wherein a solution of protected alcohol IIIB in acetone cooled to from about $-10°$ to about $25°$ C. is treated with Jones reagent (that is, $CrO_3$ dissolved or suspended in sulfuric acid in the presence of water, prepared as described in Fieser & Fieser, "Reagents for Organic Synthesis," Vol. 1, p. 142 (1967)) to form acid IV

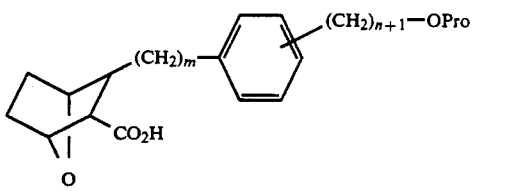

Acid IV, in an inert organic solvent, such as tetrahydrofuran, is then made to undergo a carbodiimide coupling reaction with amine hydrochloride D

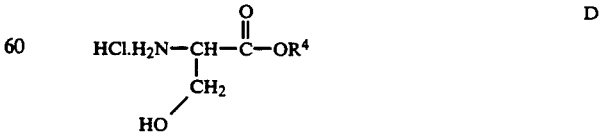

where $R^4$ is lower alkyl such as methyl or ethyl, or arylalkyl, such as benzyl, in the presence of dicyclohexylcarbodiimide (DCC) or 1-(3-dimethylaminopropyl)-3-ethylcarbodiimide hydrochloride (WSC) and 1- hydroxybenzotriazole and triethylamine under an inert atmosphere such as argon employing a molar ratio of D IV of within the range of from about 1.2:1 to about 1:1, to form hydroxyamide V

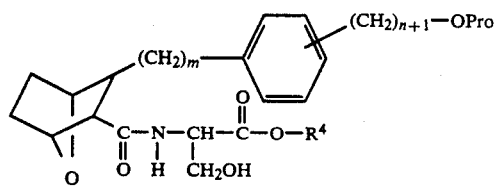

V

Hydroxyamide V is then subjected to cyclodehydration wherein a solution of V in an inert organic solvent such as tetrahydrofuran, acetonitrile or chloroform, under an inert atmosphere such as argon, is treated with triphenylphosphine (employing a molar ratio of V:triphenylphosphine of from about 0.8:1 to about 1:1) and carbon tetrachloride in the presence of an amine base such as triethylamine or diisopropylethylamine, to form oxazoline VI

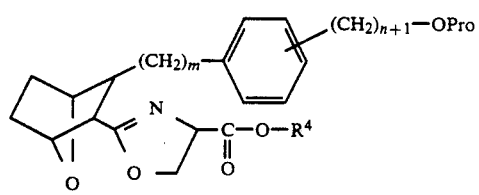

VI

Oxazoline VI is oxidized by treatment with manganese dioxide or preferably nickel peroxide (Nakagawa et al., *J. Org. Chem.*, 1962, 27, 1597) to form the oxazole VII

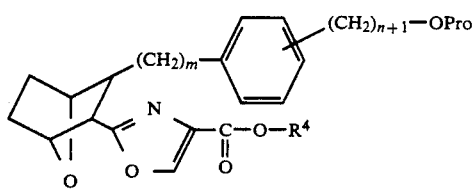

VII

Oxazole VII is converted to the corresponding acid by treating VII with a base, such as lithium hydroxide, sodium hydroxide or potassium hydroxide to form the corresponding alkali metal salt, followed by neutralization with an acid, such as dilute hydrochloric acid or oxalic acid to form acid compound VIII

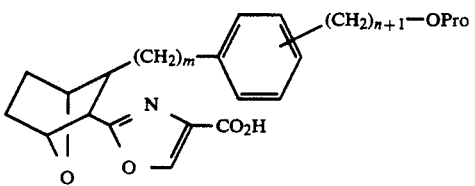

VIII

Acid VIII is converted to the corresponding acid chloride by treating VIII with oxalyl chloride optionally in the presence of catalytic amounts of dimethylformamide, and a solvent such as benzene, toluene or methylene chloride. The so-formed acid chloride is dissolved in an inert solvent such as methylene chloride or toluene cooled to a temperature within the range of from about $-10°$ C. to about $+10°$ C., and amine base such as triethylamine or pyridine and amine E, or a salt thereof, are added

E employing a molar ratio of E:VIII of within the range of from about 1.1:1 to about 1.5:1, form the oxazole IX

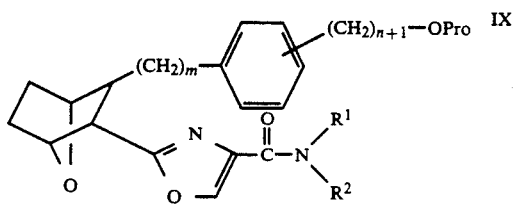

IX

Silyl ether IX is then deprotected using conventional procedures, for example, by treatment with aqueous hydrofluoric acid in the presence of acetonitrile and methylene chloride and is then subjected to a Jones oxidation employing procedures described hereinbefore to form the oxazole IGX

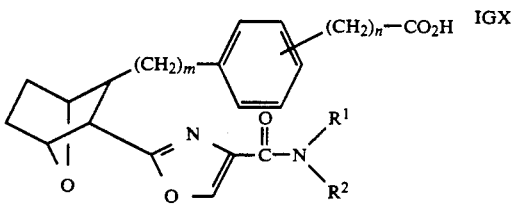

IGX

The acid IGX is then esterified by reacting IGX with a diazoalkane such as diazomethane or a strong mineral acid in alcoholic solvent, such as methanolic HCl, at a temperature within the range of from about 0° to about 25° C. to form the ester IHX.

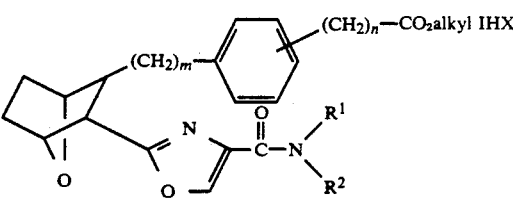

IHX

The ester IHX is then made to undergo a thionation reaction wherein ester IHX is reacted with a thionating agent such as phosphorous pentasulfide or Lawesson's reagent (2,4-bis(4-methoxyphenyl)-1,3-dithia-2,4-diphosphetane-2,4-disulfide), employing a molar ratio of thionating agent: IHX of within the range of from about 2:1 to about 10:1, and preferably from about 2:1 to about 4:1. The reaction is carried out in the presence of a weak organic base such as pyridine, triethylamine or tributylamine, and an inert organic solvent such as methylene chloride, tetrahydrofuran, at a temperature of within the range of from about 0° to about 100° C., and preferably from about 20° to about 40° C., to form the ester of the invention IH.

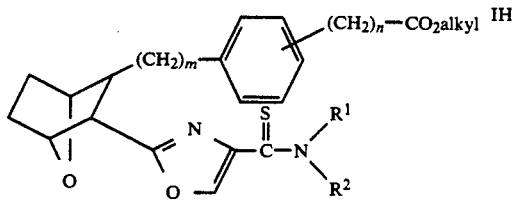

In a more preferred procedure, compounds of formula I wherein Y is a single bond, n is 1, 2, 3 or 4 and X is O may be prepared starting with alcohol III by protecting the alcohol function thereof by treatment, for example, with a solution of acetic anhydride, pyridine and 4-dimethylaminopyridine to form the protected alcohol X

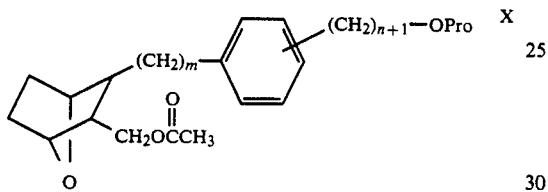

Alternatively, compound II can be protected by treatment with, for example, a solution of acetic anhydride and pyridine to form compound XI

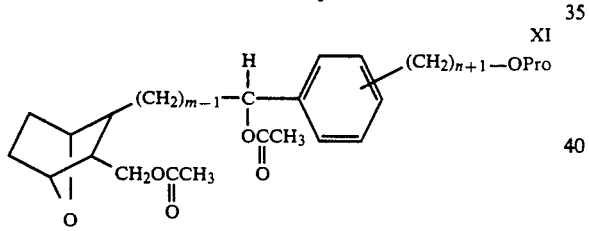

which is then subjected to hydrogenolysis as described above to provide compound X.

The protected alcohol X wherein Pro is t-butyldimethylsilyl or dimethyl(1,1,2-trimethylpropyl)silyl is subjected to a Jones oxidation employing procedures described hereinbefore to form crude acid which is deacetylated by reaction with aqueous hydroxide in the presence of inert organic solvent such as THF and then esterified, for example, by treatment with diazoalkane, such as diazomethane, or acidic alcohol such as methanolic HCl, to form the alcohol ester XII

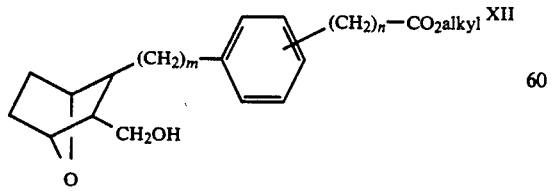

In an alternative method for forming alcohol ester XII, protected alcohol XI is subjected to a Jones oxidation and esterification to form ester XIa

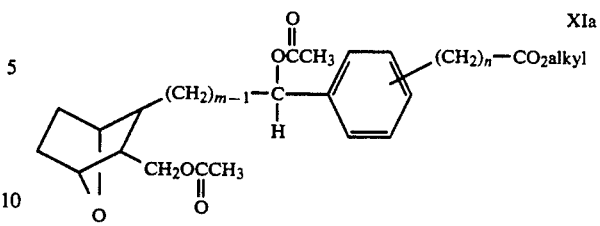

which is then made to undergo hydrogenolysis and subsequent removal of the acetate protecting group by transesterification to afford alcohol ester XII.

Next, the alcohol ester XII is subjected to a Jones oxidation to form the acid XIII

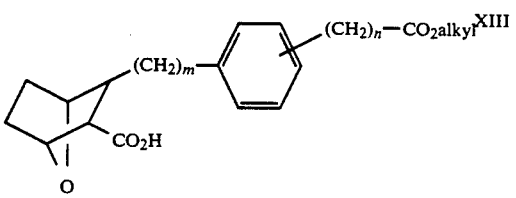

In an alternative procedure, acid XIII wherein n is 1, Z is

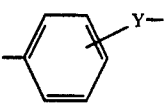

where Y is a single bond, may be prepared from alcohol III by treating III with acetic anhydride in the presence of pyridine or other organic base such as triethylamine, under an inert atmosphere such as argon, to form the corresponding acetate and treating the acetate with a deprotecting agent such as (n-$C_4H_9$)$_4$NF to remove the protecting group and form acetate alcohol IIIC

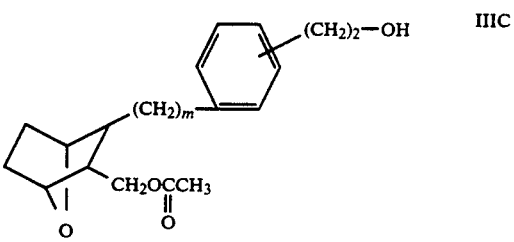

Acetate alcohol IIIC is then made to undergo a Dess-Martin oxidation by treating a mixture of IIIC in dry methylene chloride with Dess-Martin periodinane (J. Org. Chem. 1983, 48, 4155) to form the aldehyde IIID

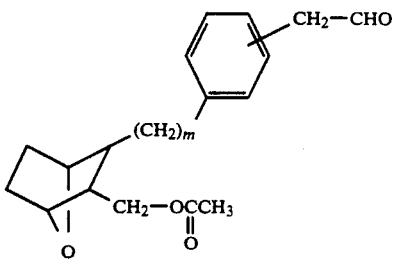

IIID which is then oxidized by treating IIID with N-iodosuccinamide (NIS) in the presence of potassium carbonate in methanol to form acetate ester IIIE

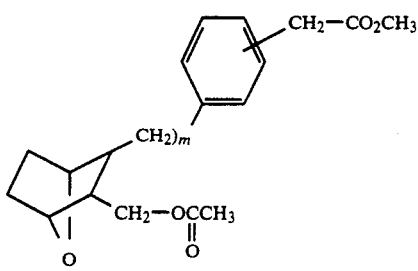

IIIE

Acetate ester IIIE in methanol is deprotected by treatment with a weak base such as potassium carbonate, and the resulting alcohol is then subjected to a Jones oxidation as described herein to form acid XIII, where n is 1.

The acid XIII is then made to undergo a carbodiimide coupling reaction with amine hydrochloride D, where $R^4$ is benzyl, as described hereinbefore (with respect to coupling of acid IV) to form the amide XIV

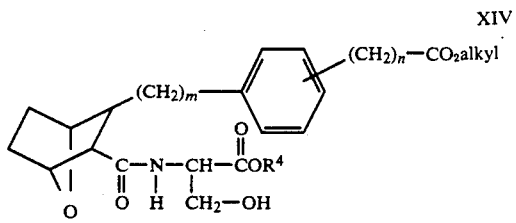

XIV

Amide XIV is then subjected to cyclodehydration (using a procedure similar to the cyclodehydration of amide V) to form oxazoline XV

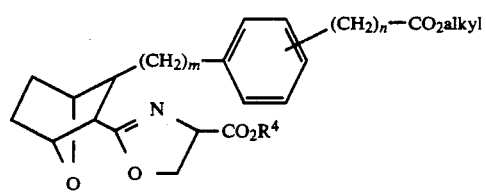

XV which is made to undergo oxidation using manganese dioxide, or nickel peroxide, or preferably cupric bromide and 1,8-diazabicyclo[5.4.0]undec-7-ene (DBU) to form the oxazole XVI

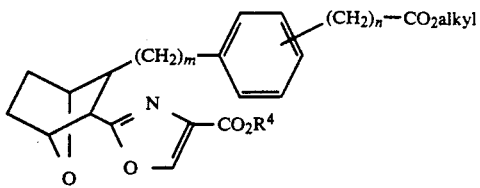

XVI

The cupric bromide oxidation is carried out at a temperature of within the range of from about 20° C. to about 70° C., employing a molar ratio of cupric bromide to XV of within the range of from about 2:1 to about 6:1 and a molar ratio of cupric bromide to DBU of within the range of from about 1 to about 1:3 in an inert solvent such as ethyl acetate or preferably ethylacetate/chloroform (1:1, v/v).

The latter oxidation is a novel method in accordance with the present invention.

Oxazole XVI is then deprotected to remove $R^4$, for example, by treatment with palladium hydroxide on charcoal and hydrogen in the presence of an inert solvent such as ethyl acetate, to form the corresponding acid XVII

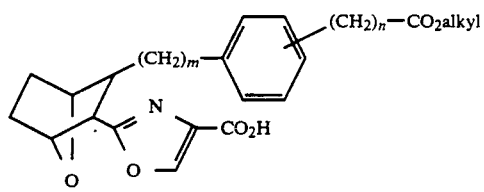

XVII

Acid XVII is then converted to the corresponding acid chloride employing a procedure similar to that described with respect to acid VIII and the resulting acid chloride is treated with amine E employing a procedure and molar ratio of E:XVII similar to that described hereinbefore with respect to acid VIII to form the ester IHX which is thionated as described hereinfore to form the corresponding ester of the invention IH.

In an alternate preferred procedure for the preparation of IH acid, XIII is made to undergo a carbodiimide coupling reaction with amine Da

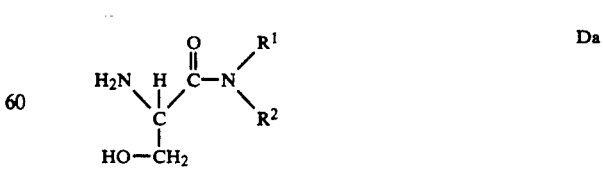

Da in the presence of dicyclohexylcarbodiimide or 1-(3-dimethylaminopropyl)-3-ethylcarbodiimide hydrochloride and 1-hydroxybenzotriazole and triethylamine as described hereinbefore to form hydroxy amide XIV'

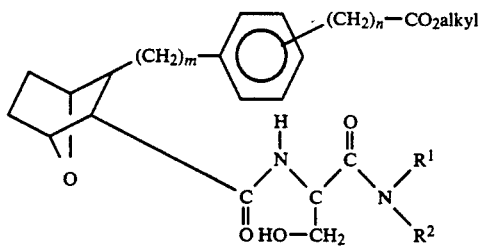

XIV'

Hydroxy amide XIV' is then subjected to cyclodehydration as described hereinbefore (with respect to the preparation of VI). A preferred method for this conversion involves treatment of XIV' with an alkylsulfonyl chloride, such as methanesulfonyl chloride in the presence of an amine such as triethylamine followed by treatment of the resulting alkylsulfonate intermediate with potassium carbonate in acetone to form oxazoline XV'

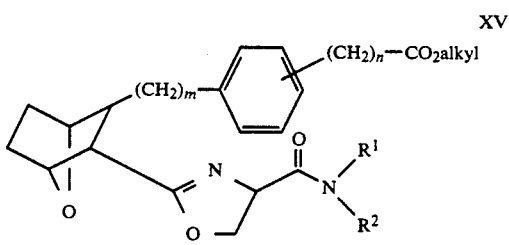

XV' which is made to undergo oxidation as described hereinbefore (with respect to the preparation of XVI) to form oxazole IHX which is then thionated as described hereinbefore to form the ester of the invention IH.

Ester IH may then be hydrolyzed by treatment with an aqueous solution of alkali metal base and then aqueous acid to form the corresponding acid IG.

Compounds of the invention wherein Y is O and X is O may be prepared as follows:

Bromophenol $A^1$

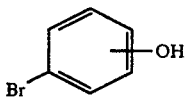

$A^1$ is treated with a protecting compound such as chloro-t-butyldimethylsilane, benzyl bromide or bromomethyl methyl ether, preferably benzyl bromide or bromomethyl methyl ether for ortho-bromophenol, employing conventional procedures to form the protected bromophenyl compound $B^1$

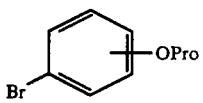

$B^1$ wherein Pro represents a protecting group.

Examples of protecting compounds suitable for use herein in reacting with bromophenol $A^1$ include those set out hereinbefore with respect to protection of alcohol A.

Protected compound $B^1$ is then transmetallated (using a procedure similar to that set out above with respect to transmetallation of B using n-butyllithium in THF) and condensed with hemiacetal C to form the condensed 7-oxabicycloheptane compound XXII

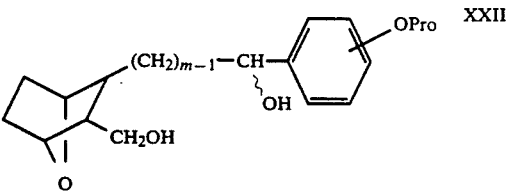

XXII

The condensed compound XXII is then subjected to hydrogenolysis by treatment with hydrogen in the presence of a catalyst such as palladium on charcoal in acetic acid, to form the alcohol XXIII in the case where Pro is a silyl or methoxymethyl ether protecting group or to form XXIV directly when Pro is benzyl.

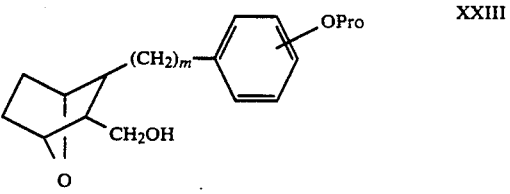

XXIII

When Pro is a silyl protecting group, compound XXIII is deprotected by treatment with, for example, a solution of acetonitrile and aqueous hydrofluoric acid to form the deprotected alcohol XXIV

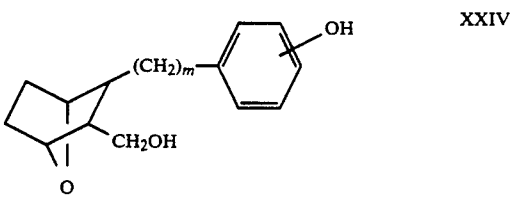

XXIV

The alcohol XXIV is then alkylated by treating a solution of alcohol XXIV in tetrahydrofuran with a molar equivalent of sodium hydride or one to four equivalents of a carbonate base such as potassium carbonate. The resulting phenoxide solution is alkylated by treating with a haloalkanoic acid ester F F Hal—$(CH_2)_n$—$CO_2$alkyl employing a molar ratio of F:XXIV of from about 1:1 to about 3:1, in the presence of an inert organic solvent such as THF or dimethylformamide or dimethoxyethane, to form ester XXV

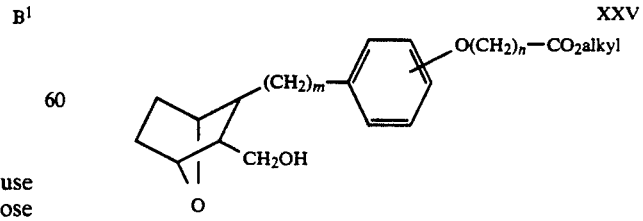

XXV

Alternatively, when the protecting group in XXIII is methoxymethyl, the free hydroxyl is protected as a benzyl ether. The methoxymethyl protecting group is removed by treatment with aqueous acid. The resulting phenol is alkylated with ethyl bromoacetate as described above for the alkylation of XXIV. The benzyl protecting group is then removed by hydrogenolysis with palladium hydroxide and hydrogen to give XXV.

Alternatively, alcohol ester starting materials of formula XXV may be prepared by following the procedure as described in U.S. Pat. No. 4,536,513.

Next, the alcohol ester XXV is subjected to a Jones oxidation as described hereinbefore with respect to the oxidation of alcohol IIIB, to form acid XXVI

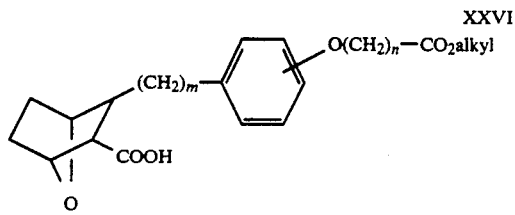

The acid XXVI is then used to prepare compounds of the invention of formula IJ and IK using the procedures set out hereinbefore with respect to conversion of acid XIII to ester IH

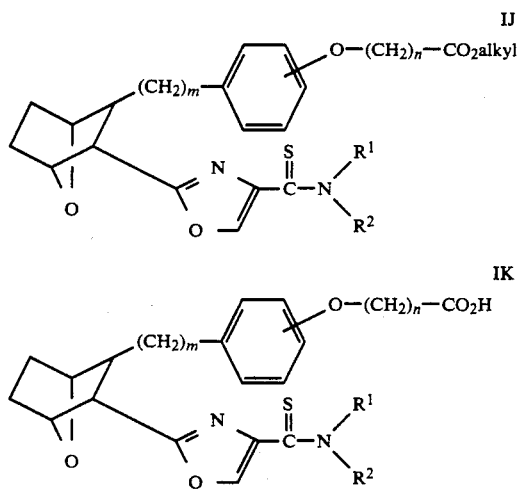

Compounds of the invention wherein Y is a single bond or O and X is S may be prepared starting with acid XIII or XXVI as follows:

Acid XIII or XXVI is reacted with oxalyl chloride, optionally in the presence of catalytic amounts of dimethylformamide, in methylene chloride, to form the corresponding acid chloride which is amidated by reacting with ammonia to form the amide XXVII

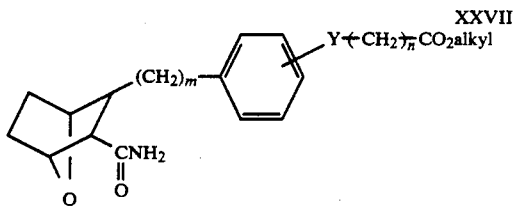

Alternatively, acid XIII or XXVI is reacted with an alkylchloroformate in the presence of an amine- such as triethylamine to form the mixed anhydride which is amidated by reacting with methanol-ammonia solution or concentrated aqueous ammonia solution to form amide XXVII.

Amide XXVII is then treated with phosphorus pentasulfide ) or Lawesson's Reagent (2,4-bis(4-methoxyphenyl)-1,3-dithia-2,4-diphosphetane-2,4-disulfide) to form the corresponding thioamide XXVIII

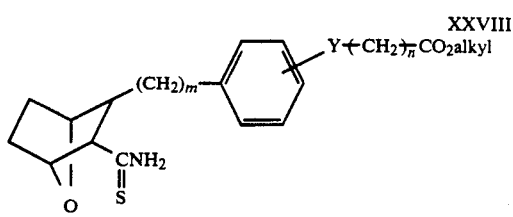

which is treated with bromopyruvic acid

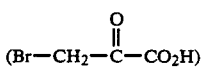

in a polar solvent such as dimethylformamide in the presence of a weak base such as $K_2CO_3$ employing a molar ratio of XXVIII: bromopyruvic acid of within the range of from about 1:1 to about 1:1.5 to form thiazoline XXIX

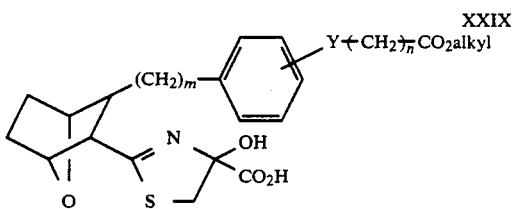

Thiazoline XXIX is then dehydrated by treatment with a sulfonyl chloride such as methanesulfonyl chloride in the presence of a base such as triethylamine to form thiazole acid XXX

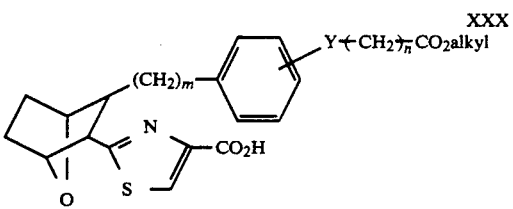

which is then made to undergo a carbodiimide coupling reaction with amine

in the presence of DCC or WSC under an inert atmosphere such as argon employing a molar ratio of E:XXX of within the range of from about 1:1 to about 2:1, to form amide ILX which is subjected to thionation as described hereinfore to form ester of the invention IL

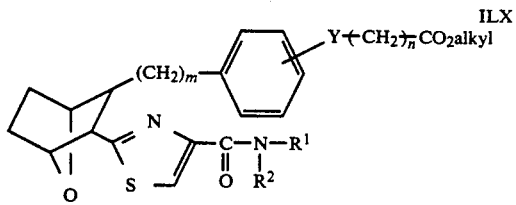

ILX

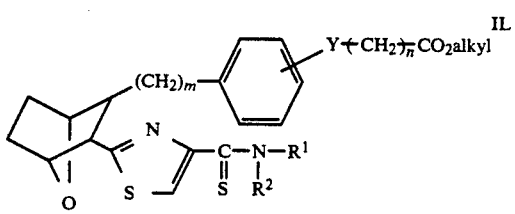

IL

Alternatively, acid XXX can be activated by conversion to the corresponding acid chloride by treating acid XXX with oxalyl chloride in a nonpolar solvent such as benzene. The acid chloride is then coupled with amine E using an amine base such as triethylamine or pyridine to form ILX which is then subjected to thionation as described hereinbefore to form ester IL.

Compounds of the invention where Y is a single bond or O and X is NH are prepared starting with acid XIII or XXVI which is made to undergo a coupling reaction with amine G

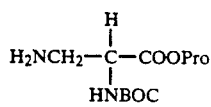

G where BOC is t-butyloxycarbonyl and Pro is a protecting group such as benzyl, in the presence of a coupling agent such as 1-(3-dimethylaminopropyl)-3-ethylcarbodiimide hydrochloride (WSC) and 1-hydroxybenzotriazole (HOBT) and methylene chloride employing a molar ratio of XIII or XXVI:G of within the range of from about 1.2:1 to about 1:1, for a period of from about 12 to about 90 hours. The resulting amide is made to undergo a thionation reaction by treating the amide with Lawesson's reagent in the presence of benzene at a temperature of from about 50° to about 75° C. for a period of from about 1 to about 4 hours, to form the ester XXXI

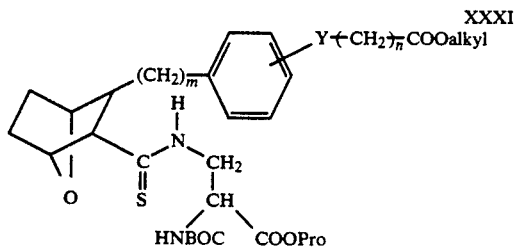

XXXI

The ester XXXI is cyclized by treating a solution of XXXI in an inert solvent such as acetonitrile, chloroform or tetrahydrofuran with triphenylphosphine (employing a molar ratio of XXXI:triphenylphosphine of from about 0.8:1 to about 1:1) and carbon tetrachloride in the presence of an amine base such as triethylamine or diisopropylethylamine, to form imidazoline XXXII

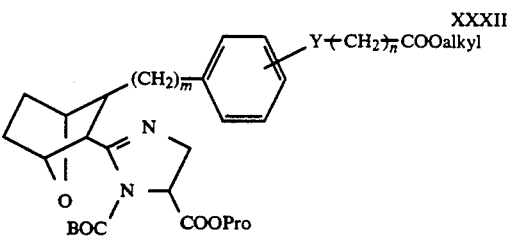

XXXII

Imidazoline XXXII is then deprotected to remove the Pro protecting group, using conventional procedures for example, by hydrogenation when Pro is benzyl, to form the acid XXXIII

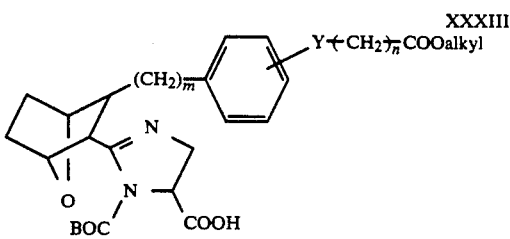

XXXIII

Next, the acid XXXIII is made to undergo a coupling reaction with amine E in the presence of an amine base such as pyridine or triethylamine under an inert atmosphere such as argon in the presence of a coupling agent such as WSC and HOBT and chloroform, employing a molar ratio of E:XXXIII of within the range of from about 0.8:1 to about 1.2:1 to form amide XXXIV

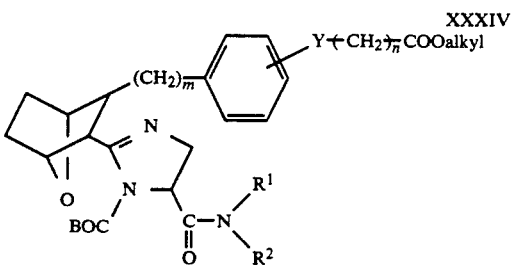

XXXIV

The amine XXXIV in solution in methylene chloride is then treated with trifluoroacetic acid to remove the BOC group and form amide XXXV

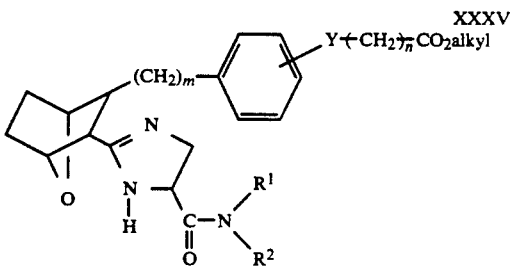

XXXV

Amide XXXV is oxidized by treatment with an oxidizing agent such as manganese dioxide in the presence of an inert solvent such as chloroform to form ester IMX

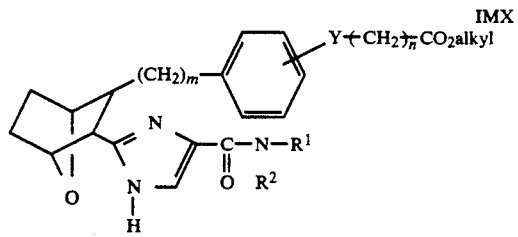

IMX

The ester IMX is then subjected to thionation as described hereinbefore to form the corresponding ester IM of the invention

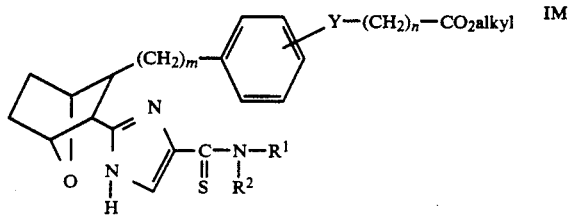

IM

Compounds of the invention wherein n is 0 and Y is a single bond, that is benzoic acids or derivatives thereof of the structure IN

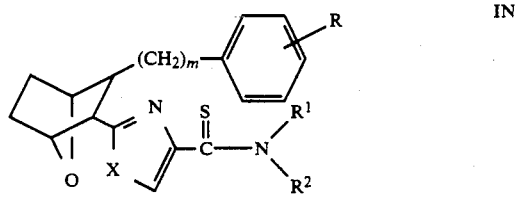

IN may be prepared starting with bromobenzyl alcohol $A^2$

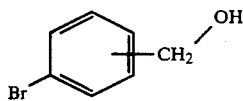

$A^2$ which is treated with a protecting compound such as t-butylchlorodiphenylsilane, in the presence of 4-dimethylaminopyridine and an amine base such as triethylamine and an inert solvent, such as methylene chloride, employing conventional procedures, to form the protected bromobenzyl compound $B^2$

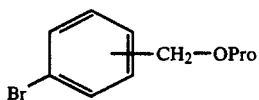

$B^2$ wherein Pro represents a protecting group.

Examples of protecting compounds suitable for use herein with the exclusion of benzyl bromide are as set out hereinbefore in reacting with bromophenalkyl alcohol A.

The protected compound $B^2$ is then transmetallated by treatment with t-$C_4H_9$Li or n-$C_4H_9$Li in the presence of diethyl ether or tetrahydrofuran at reduced temperature of from about $-100°$ to about $0°$ C. (or is subjected to a Grignard reaction by treatment with magnesium in the presence of an inert organic solvent such as tetrahydrofuran (THF) or diethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

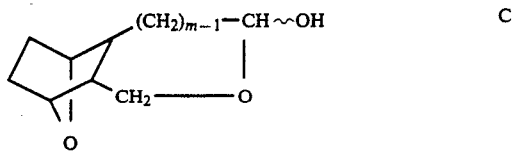

C employing a molar ratio of C:$B^2$ of within the range of from about 1:2 to about 1:4, in the presence of an inert organic solvent such as THF at a reduced temperature of from about $-78°$ to about $25°$ C., to form the condensed 7-oxabicycloheptane compound IIA

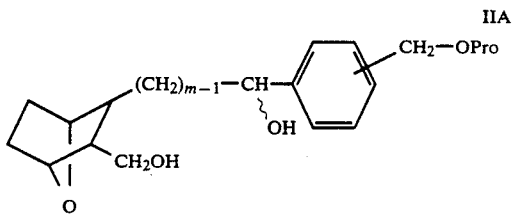

IIA

Compound IIA is then protected by treatment with, for example, a solution of acetic anhydride and pyridine in the presence of 4-dimethylaminopyridine to form compound XIA

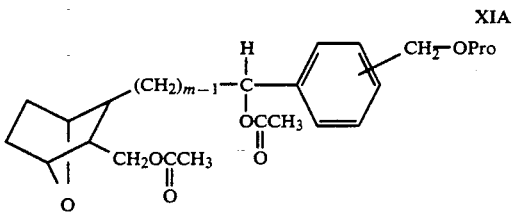

XIA

The protected alcohol XIA is then deprotected using conventional procedures and the resulting alcohol subjected to a Jones oxidation employing procedures described hereinbefore to form crude acid. The crude acid is deacetylated by reaction with aqueous hydroxide in the presence of inert organic solvent such as THF and then esterified, for example, by treatment with diazoalkane, such as diazomethane, or acidic alcohol, to form the alcohol ester XIIA

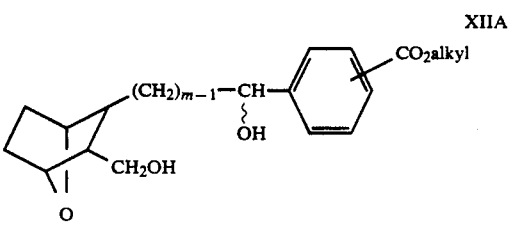

XIIA

The alcohol ester is then subjected to hydrogenolysis as described above to provide alcohol ester compound XIIB

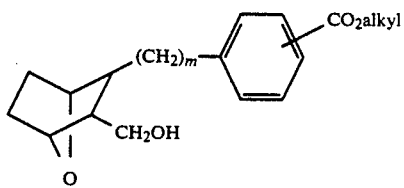

XIIB

Next, the alcohol ester XIIB is subjected to a Jones oxidation to form the acid XIIIA

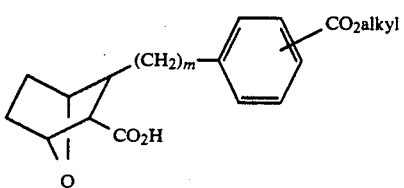

XIIIA which may be used in place of acid XIII to form compounds of the invention of the formula IH'

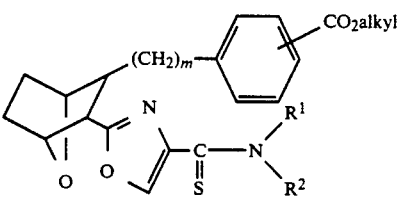

IH'

In a preferred method, compounds of the invention wherein n is 0, m is 1 and Y is a single bond, and R is in the ortho position, that is benzoic acids or derivatives thereof of the structure INa

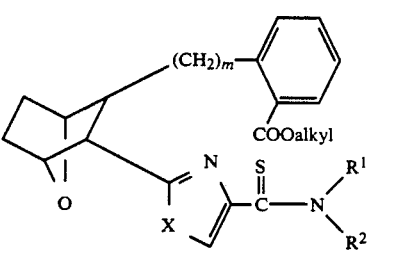

INa may be prepared starting with oxazoline $B^3$

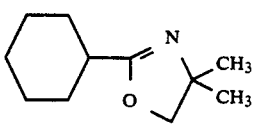

$B^3$ (prepared as described by A. I. Meyers et al. in J. Org. Chem. 39, 2787 (1974)) which is metallated by treatment with t-$C_4H_9Li$ or n-$C_4H_9Li$ in the presence of diethyl ether or tetrahydrofuran at reduced temperature of from about $-100°$ to about $0°$ C. and then is condensed with (exo)octahydro-4,7-epoxyisobenzofuran-1-ol (prepared as described in U.S. Pat. No. 4,143,054) of the structure Ca

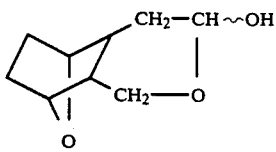

Ca employing a molar ratio of Ca:$B^3$ of within the range of from about 1:2 to about 1:4, in the presence of an inert organic solvent such as THF at a reduced temperature of from about $-78°$ to about $0°$ C., to form the condensed 7-oxabicycloheptane compound IIA'

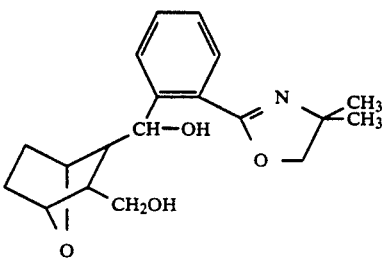

IIA'

Compound IIA' is then subjected to aqueous acidic hydrolysis by treatment with aqueous oxalic acid to form compound XIA'

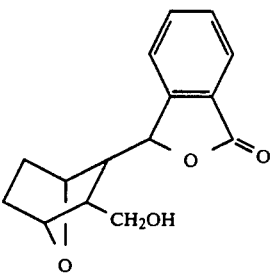

XIA'

XIA' is then subjected to hydrogenolysis as described above and esterification to provide alcohol ester compound XIIB'

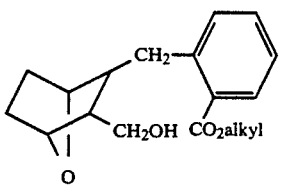

XIIB'

Compound XIIB' may be used in place of XIIB to form acid XIIIA'

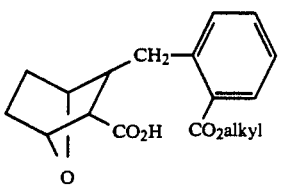

XIIIA'

The acid XIIIA or XIIIA' is then used in place of acid XIII to form the corresponding benzoic acids of structure IOX

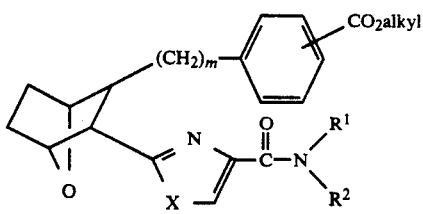
IOX including

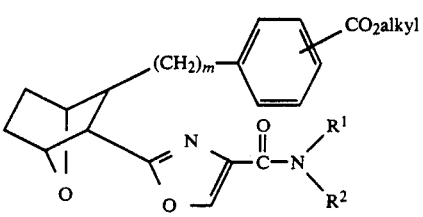
IPX

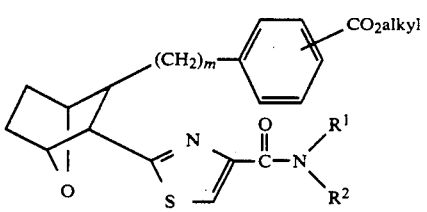
IQX

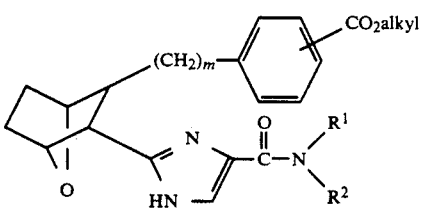
IRX each of which may be subjected to thionation as described hereinbefore to form the corresponding thionated esters of the invention (IO, IP, IQ and IR, not shown).

Compounds of formula I wherein Z is

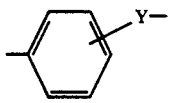

and Y is —CH=CH— may be prepared starting with alcohol XII wherein n is 2 which is treated with a silane protecting compound as described hereinbefore in the presence of an amine base, such as triethylamine and an inert solvent such as methylene chloride and N,N-dimethylaminopyridine (DMAP) to form the protected alcohol XIIa.

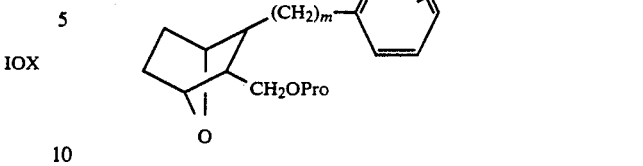
XIIa

The protected alcohol XIIa is then treated with lithium diisopropylamide in the form of a cooled (−78° to 0° C.) mixture of diisopropylamine and t-butyllithium or n-butyllithium, under argon. The resulting mixture is treated with diphenyl diselenide at a temperature of within the range of from about −78° to about 25° C., to form the corresponding selenide

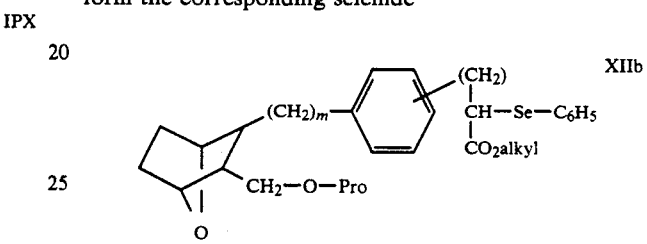
XIIb

Selenide XIIb in an inert organic solvent such as ethyl acetate and/or methanol is treated with an oxidizing agent such as aqueous hydrogen peroxide to form the cinnamate XIIc

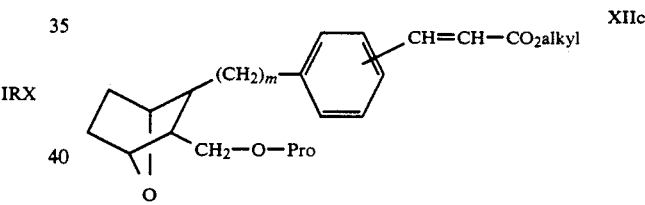
XIIc

The protecting group is removed from XIIc by treating XIIc with acetyl chloride in the presence of an organic solvent such as methanol to form the alcohol XIId

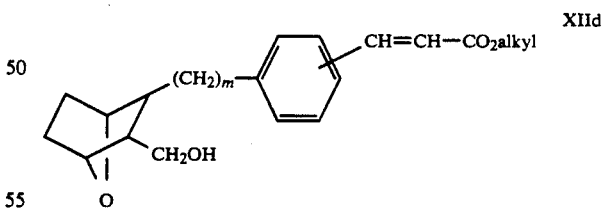
XIId

Alcohol XIId may then be employed to form compounds of formula I wherein Z is

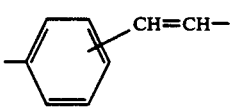

employing procedures described hereinbefore. The starting bromophenylalkyl alcohol A where n is 2 may be prepared by subjecting aldehyde M to a Wittig reaction with $(C_6H_5)_3PCHCO_2CH_3$ to form the ester N

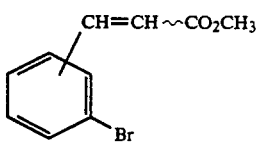
N which is made to undergo a double bond reduction by treatment with hydrogen in the presence of rhodium on alumina catalyst in the presence of methanol to form ester O

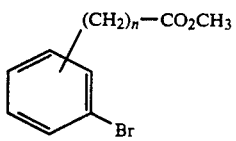
O

Ester O is then reduced by treatment with diisobutylaluminum hydride in the presence of toluene solvent to form alcohol A.

The compounds of formula I of the invention wherein Z is —CH=CH or —(CH$_2$)$_2$— may be prepared as follows.

Compounds of the invention where Z is —CH=CH— and preferably in the cis form, and X is O are prepared starting with the hydroxymethyl compound AA

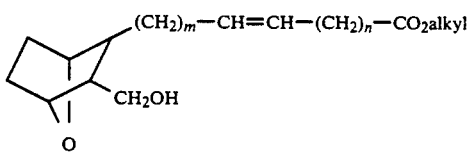
AA (which is prepared as described in U.S. Pat. No. 4,143,054) which is subjected to a Jones oxidation wherein AA is reacted with Jones' Reagent (CrO$_3$ dissolved or suspended in aqueous sulfuric acid, prepared as described in Fieser & Fieser, "Reagents for Organic Synthesis", Vol I, p. 142 (1967)) in the presence of acetone, under an inert atmosphere such as argon at a temperature within the range of from about −10° to about 20° C., to form the corresponding carboxylic acid BB

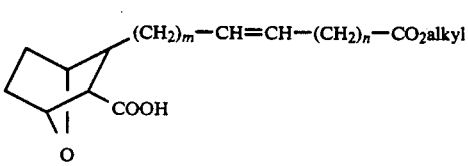
BB

Acid BB, in an inert organic solvent, such as tetrahydrofuran, is then made to undergo a carbodiimide coupling reaction with amide Da

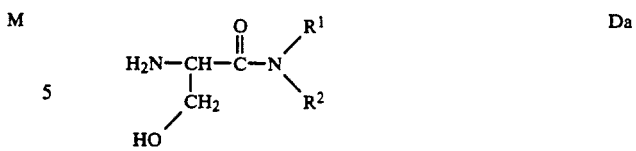
Da in the presence of dicyclohexylcarbodiimide (DCC) or 1-(3-dimethylaminopropyl)-3-ethylcarbodiimide hydrochloride (WSC) and 1-hydroxybenzotriazole under an inert atmosphere such as argon employing a molar ratio of Da:BB of within the range of from about 1.2:1 to about 1:1, to form hydroxybisamide IIa

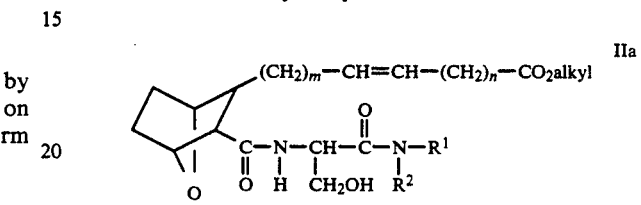
IIa

Hydroxybisamide IIa is then subjected to cyclodehydration wherein a solution of IIa in an inert organic solvent such as tetrahydrofuran, acetonitrile or chloroform, under an inert atmosphere such as argon, is treated with triphenylphosphine and carbon tetrachloride in the presence of an amine base such as triethylamine, to form oxazoline IIIa.

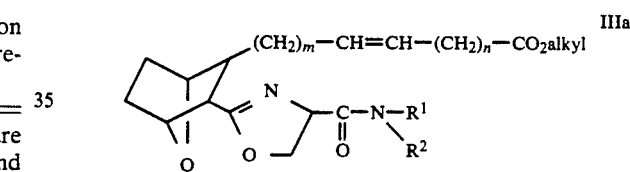
IIIa

Alternatively, hydroxybisamide IIa is treated with a sulfonyl chloride, such as methane sulfonyl chloride, and an amine base such as triethylamine followed by treatment with potassium carbonate in acetone to form oxazoline IIIa.

Oxazoline IIIa is oxidized by treatment with manganese dioxide or nickel peroxide preferably nickel peroxide to form the oxazole IDa

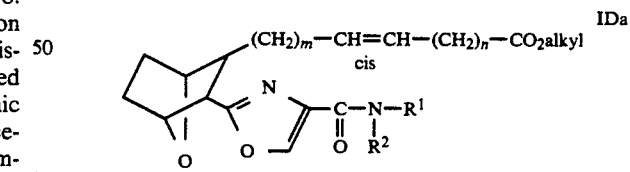
IDa

Alternatively, oxazole IDa can be prepared from acid BB

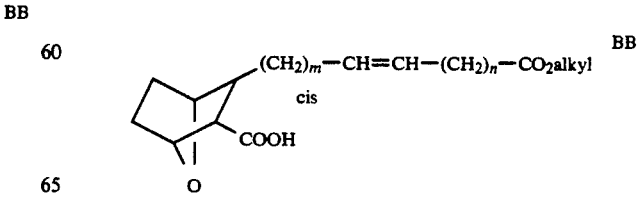
BB by a carbodiimide coupling as described previously except substituting CCa for Da to obtain IIb.

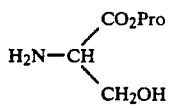

CCa

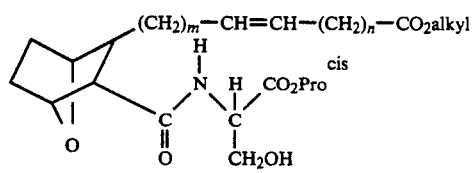

where Pro is a conventional protecting group. Hydroxyamide IIb is then subjected to a cyclodehydration and oxidation as described for IIa and IIIa to form ID'

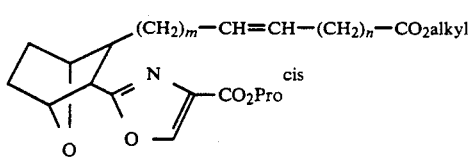

The protecting group of ID' can be removed to form the corresponding acid ID'' which is treated with excess

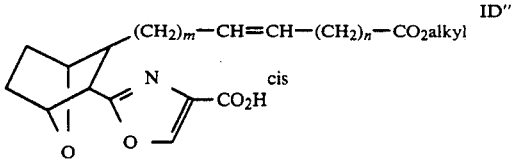

oxalyl chloride in the presence of an inert organic solvent such as toluene, methylene chloride, or chloroform, and optionally a catalytic amount of dimethylformamide, while stirring under an inert atmosphere such as argon, to form the crude acid chloride IDa''

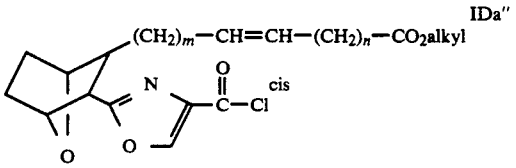

which is treated with amine hydrochloride E'

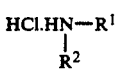

E' in the presence of an organic base such as triethylamine under an inert atmosphere such as argon, employing a molar ratio of IDa'':E' of within the range of from about 0.5:1 to about 2:1 and preferably from about 0.8:1 to about 1:1, to form IDa'''

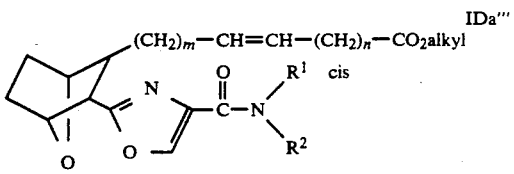

which is thionated as described hereinbefore to form the corresponding thioamide IDa$^x$ of the invention

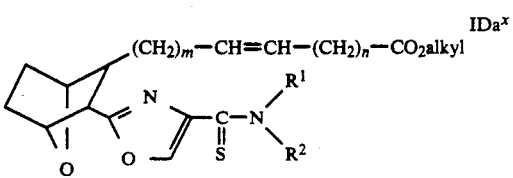

Compounds of formula I wherein Z represents —CH=CH— which is the trans double bond isomer may be prepared starting with hydroxymethyl compound AA which includes a cis double bond. Compound AA is treated with a protecting compound such as t-butyldimethylsilyl chloride or other silyl protecting group as described hereinbefore in the presence of imidazole or triethylamine and an inert organic solvent such as methylene chloride or tetrahydrofuran, to form the protected compound AA'

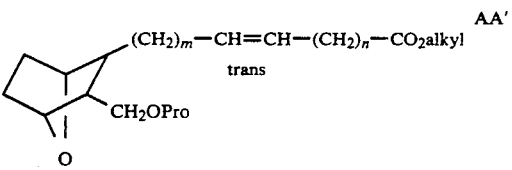

A solution of the protected alcohol in an inert organic solvent such as methylene chloride or acetone is treated with excess ozone at reduced temperature of from about $-78°$ to about $-60°$ C. followed by treatment with dimethyl sulfide (molar ratio of AA':(CH$_3$)$_2$S of within the range of from about 0.01:1 to about 0.2:1), to form the aldehyde AA$^2$

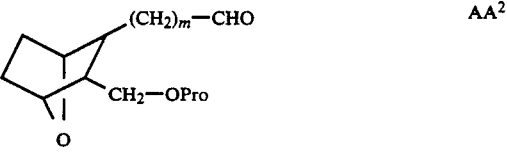

Aldehyde AA$^2$ is then treated with a mixture of lithium bromide or lithium chloride and trimethylphosphonoacetate and triethylamine in an inert organic solvent such as methylene chloride or chloroform to form the ester AA$^3$

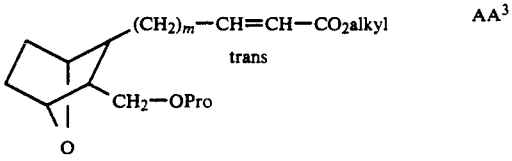

A solution of ester AA³ in an inert organic such as tetrahydrofuran, diethyl ether or dimethyoxyethane is cooled to a temperature of from about −78° to 0° C. and reacted with diisobutylaluminum hydride in an aromatic solvent such as toluene for a period of from about 0.5 to about 4 hours to form alcohol AA⁴

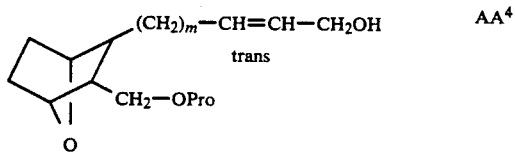

Alcohol AA⁴ is treated with bromotriphenylphosphonium bromide (formed by adding bromine to triphenylphosphine in toluene or other aromatic solvent under an inert atmosphere such as argon, at a reduced temperature of from about −10° to about 10° C.) in the presence of pyridine and toluene, at a reduced temperature of from about −10° to about 10° C., to form bromide AA⁵

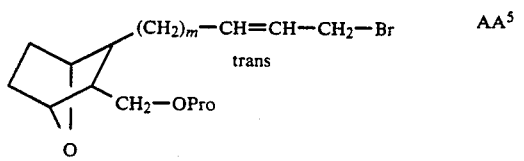

An acetic acid ester such as t-butyl acetate or ethyl acetate is treated with a solution of LDA (lithium diisopropylamide) in an inert organic solvent such as tetrahydrofuran and at a reduced temperature of from about −78° to about −60° C. for a period of from about 0.5 to about 2 hours followed by addition of a solution of bromide AA⁵ in an inert solvent such as tetrahydrofuran to form ester AA⁶ (n is 2)

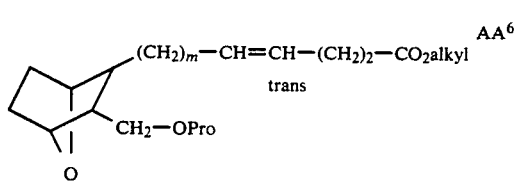

For compounds of the invention where Z=—CH═CH— in the trans form and n is 1, 3, or 4, aldehyde XI is allowed to react with a phosphonium salt of formula P

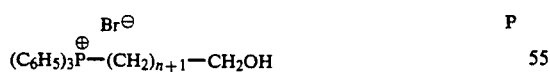

in the presence of a strong base such as potassium t-amylate in toluene or NaH/dimethylsulfoxide to give XIII'

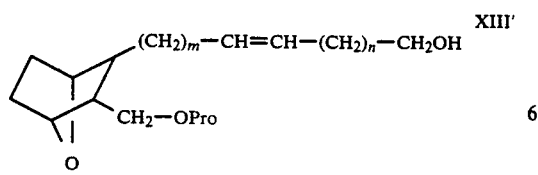

which is oxidized and esterified using procedures known to those skilled in the art to form ester AA⁶ (where n=1, 3, or 4).

Ester AA⁶ is then deprotected by treating AA⁶ in methanol under an inert atmosphere such as argon with hydrochloric acid in methanol (prepared by adding acetyl chloride to methanol) to form alcohol AA⁷

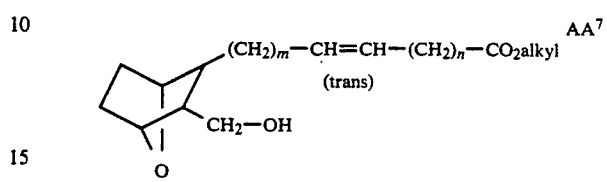

AA⁷ may then be used in place of AA as a starting material following the procedure hereinbefore described to form acid AA⁸

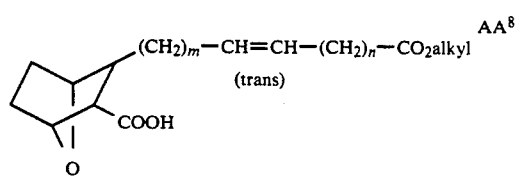

and subsequently to form the trans compound of formula IDaa of the invention

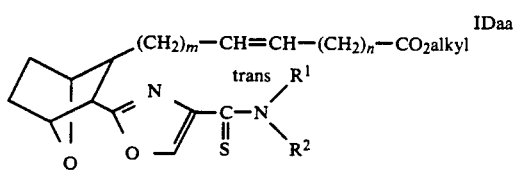

Compounds of the invention IB wherein Z is —CH═CH— and X is S may be prepared starting with acid BB or AA⁸ as follows:

Acid BB or AA⁸ is reacted with oxalyl chloride, optionally in the presence of catalytic amounts of dimethylformamide, in methylene chloride, to form the corresponding acid chloride which is amidated by reacting with ammonia to form the amide XXXVII

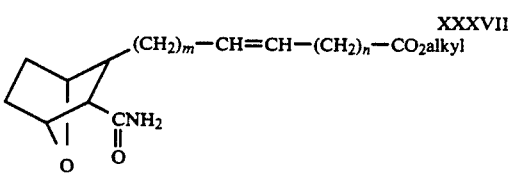

Alternatively, acid BB or AA⁸ is reacted with an alkylchloroformate in the presence of an amine such as triethylamine to form the mixed anhydride which is amidated by reacting with methanol-ammonia solution or concentrated aqueous ammonia solution to form amide XXXVII.

Amide XXXVII is then treated with phosphorus pentasulfide or Lawesson's Reagent (2,4-bis(4-methoxyphenyl)-1,3-dithia-2,4-diphosphetane-2,4-disulfide) to form the corresponding thioamide XXXVIII of from about 0.8:1 to about 1.2:1 to form amide XLIV

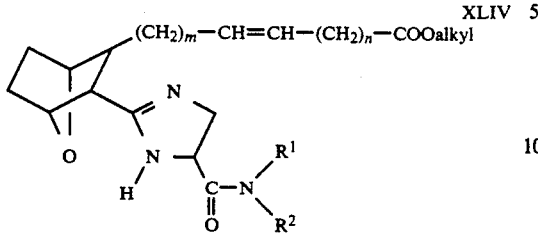
XLIV

Amide XLIV is oxidized by treatment with an oxidizing agent such as manganese dioxide in the presence of an inert solvent such as chloroform to form ester IFb

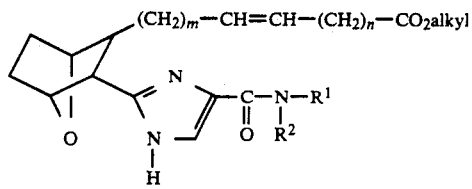
IFb which is thionated as described hereinbefore to form the corresponding thioamide of the invention.

The aforementioned thioamide esters of the invention may be converted to the corresponding thionated acids, that is IS

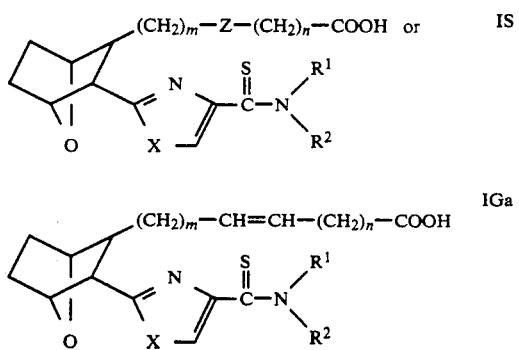
IS

IGa by treating the thioamide esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention.

Compounds of formula I wherein Z is —(CH$_2$)$_2$— may be prepared from alcohol AA by subjecting AA to hydrogenation using, for example, a hydrogenation catalyst, such as palladium on carbon or Wilkinson's catalyst, in an inert organic solvent such as ethyl acetate (EtOAc) or benzene or by diimide reduction and substituting the resulting product for AA in the sequences outlined hereinbefore to prepare IGa, to form acid of invention IGa'.

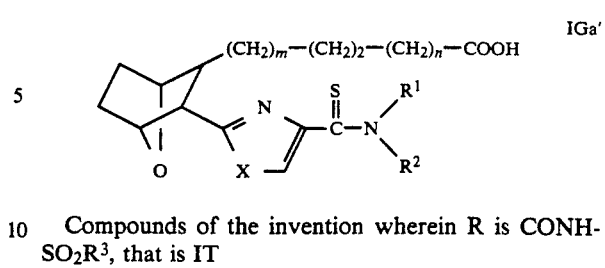
IGa'

Compounds of the invention wherein R is CONH-SO$_2$R$^3$, that is IT

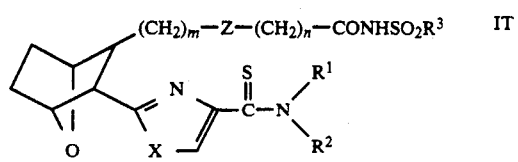
IT are prepared by treating acid IS, IGa or IGa' with a sulfonamide of the structure H

H in the presence of a coupling agent such as carbonyldiimidazole or WSC in the presence of an amine such as dimethylaminopyridine under an inert atmosphere such as argon employing a molar ratio of H:IS or IG, or IGa' of within the range of from about 0.8:1 to about 1.2:1, to form sulfonamide IT.

Acids IS, IGa and IGa' may be converted to the corresponding alkyl esters by treating the acids IS, IGa and IGa' with the appropriate alcohol under acid catalysis to form the esters.

Compounds of the invention wherein R is

—CH$_2$-5-tetrazolyl, Z is 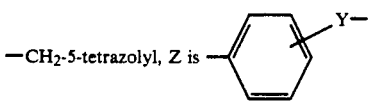

and Y is a single bond, or E is —(CH$_2$)$_2$— that is IU where Y is a single bond

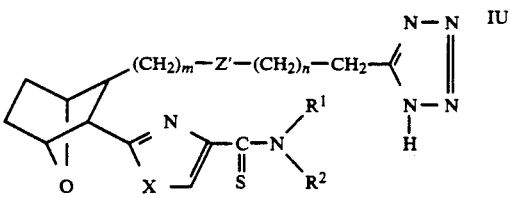
IU where Z' is

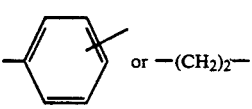 or —(CH$_2$)$_2$— are prepared by subjecting esters IH, IJ, IL, IM, IP, IMa, IQ or IR or the esters of IS, IGa or IGa' where Z is

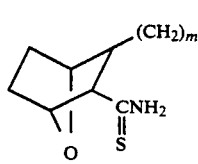   XXXVIII which is treated with bromopyruvic acid

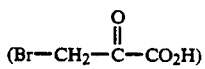

in a polar solvent such as dimethylformamide in the presence of a weak base such as $K_2CO_3$ employing a molar ratio of XXXVIII: bromopyruvic acid of within the range of from about 1:1 to about 1:1.5 to form thiazoline XXXIX

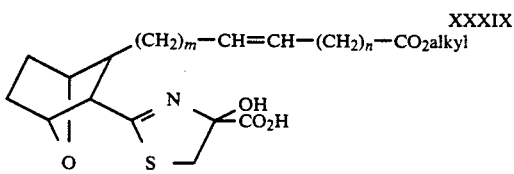   XXXIX

Thiazoline XXXIX is then dehydrated by treatment with a sulfonyl chloride such as methanesulfonyl chloride in the presence of a base such as triethylamine to form thiazole acid XL

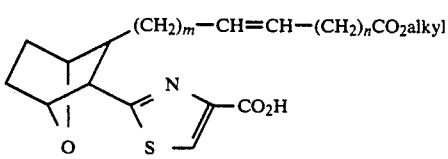   XL which is then made to undergo a carbodiimide coupling reaction with amine

   A''' in the presence of DCC or WSC under an inert atmosphere such as argon employing a molar ratio of A''':XL of within the range of from about 1:1 to about 2:1, to form amide $IF_a$

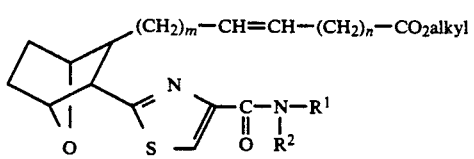   $IF_a$ which is thionated as described hereinbefore to form the corresponding thioamide of the invention.

Compounds of the invention EI where X is NH and $Z^1$ is —CH=CH— are prepared starting with acid BB or $AA^8$ which is made to undergo a coupling reaction with amine Q

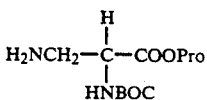   Q where Boc is t-butyloxycarbonyl and Pro is a protecting group such as preferably —$CH_2CH_2Si(CH_3)_3$, in the presence of a coupling agent such as 1-(3-dimethylaminopropyl)-3-ethylcarbodiimide hydrochloride (WSC) and 1-hydroxybenzotriazole (HOBT) and methylene chloride employing a molar ratio of BB or $AA^8$:Q of within the range of from about 1.2:1 to about 1:1, for a period of from about 12 to about 90 hours. The resulting amide is made to undergo a thionation reaction by treating the amide with Lawesson's reagent in the presence of benzene at a temperature of from about 50° to about 75° C. for a period of from about 1 to about 4 hours, to form the ester XLI

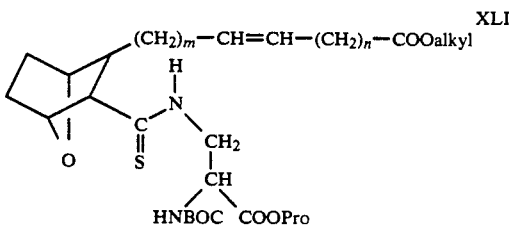   XLI

The ester XLI is cyclized by treating a solution of XLI in an inert solvent such as acetonitrile, chloroform or tetrahydrofuran, with triphenylphosphine (employing a molar ratio of XLI:triphenylphosphine of from about 0.8:1 to about 1:1) and carbon tetrachloride in the presence of an amine base such as triethylamine or diisopropylethylamine, to form imidazoline XLII

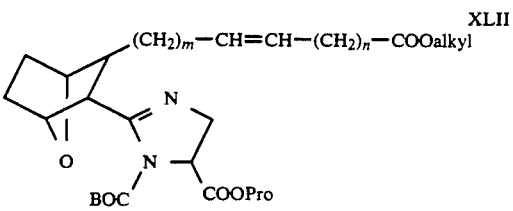   XLII

Imidazoline XLII is then deprotected to remove the Pro protecting group, using conventional procedures, for example, by treatment with trifluoroacetic acid in the presence of methylene chloride, to form the acid XLIII

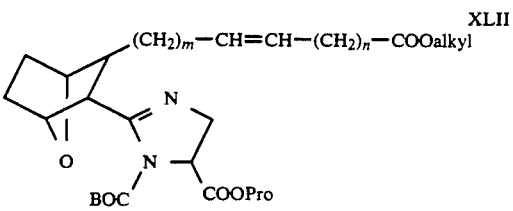   XLIII

Next, the acid XLIII is made to undergo a coupling reaction with amine A''' in the presence of an amine base such as pyridine or triethylamine under an inert atmosphere such as argon in the presence of a coupling agent such as WSC and HOBT and chloroform, employing a molar ratio of A''':XLIII of within the range

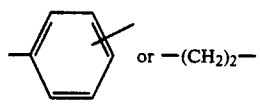

to reduction with a hydride reagent such as lithium borohydride or sodium borohydride to afford alcohol XXXVIIA

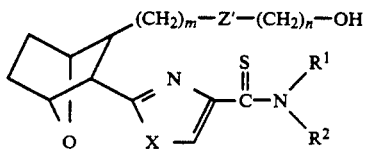

which is converted to the bromide on treatment with triphenylphosphonium dibromide in an inert solvent such as toluene. The bromide is then converted to nitrile XXXVIIIA on treatment with an alkali metal cyanide in a polar solvent such as methanol/water.

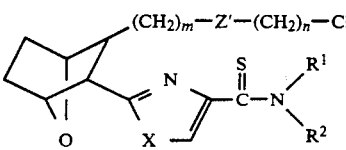

The nitrile XXXVIIIA is then subjected to a cycloaddition reaction by treating XXXVIIIA with sodium azide in the presence of ammonium chloride, dimethylformamide and lithium chloride at a temperature of from about 100° C. to about 130° C. to form IU.

Compounds of the invention wherein R is —CH$_2$-5-tetrazolyl and Y=O, that is IU where Y is O, are prepared by conversion of alcohol XXIII to ether XXXIXA using the procedures set out hereinbefore for the conversion of XII to esters IE, IH and IJ

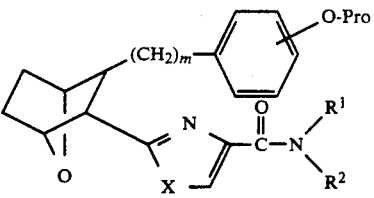

which is converted to the corresponding nitrile by deprotection, for example with aqueous HF, followed by alkylation with halonitrile J in the J  X—(CH$_2$)$_n$—CN presence of a base such as sodium hydride or potassium carbonate, and thionation as described hereinbefore.

The nitrile is then subjected to a cycloaddition reaction by treating with sodium azide in the presence of ammonium chloride, dimethylformamide and lithium chloride at temperatures from about 100° C. to about 130° C. to form IU.

Compounds of the invention wherein R is —CH$_2$-5-tetrazolyl, that is IJa

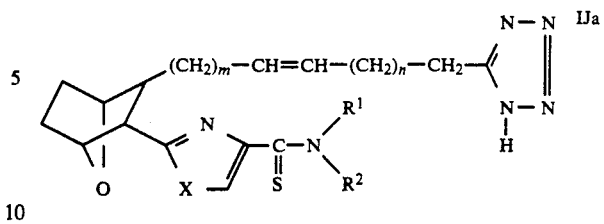

are prepared by treating alcohol Ca (prepared as described in U.S. Pat. No. 4,654,356)

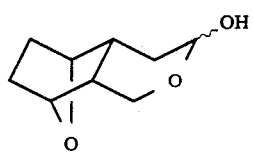

with a Wittig reagent of the structure La

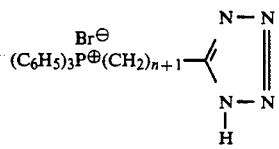

in the presence of a base, such as potassium t-butoxide or sodium hydride-dimethyl sulfoxide employing a molar ratio of Ca:La of within the range of from about 1:1 to about 0.2:1 to form the hydroxymethyl compound XIIa

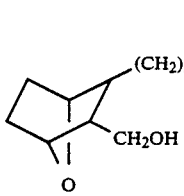

which is treated with protecting compound Ma

Ma  Pro-Halide for example, bromomethyl methyl ether to form the protected tetrazole XIIIa

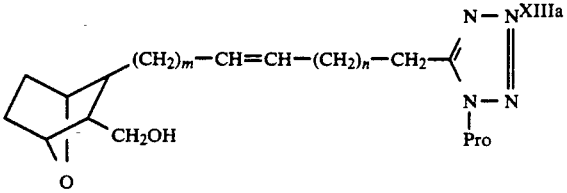

The protected tetrazole XIa may then be used in place of hydroxymethyl compound AA to form the various compounds of the formula XIVa wherein X is O, S or NH

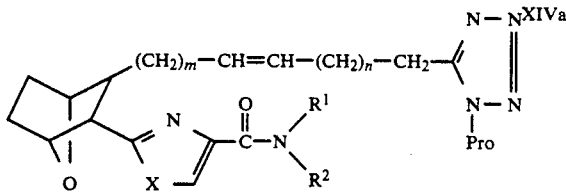

which is deprotected by treatment with aqueous acid such as aqueous hydrochloric acid, followed by thionation as described hereinbefore, to form compounds of the invention IJa.

Compounds of formula I wherein R is CONHR$^{3a}$ wherein R$^{3a}$ is other than H may be prepared from the corresponding acid

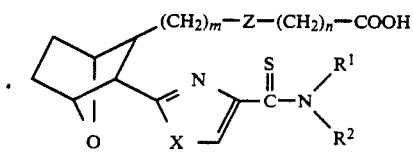

by treating acid I$_1$ with WSC in the presence of dimethylformamide and HOBT, organic basic such as triethylamine and amine E″

E″ HNHR$^{3a}$ to form the amide of the invention I$_2$

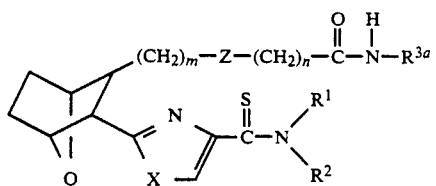

where R$^{3a}$ is lower alkyl, aryl or aralkyl.

Compounds of formula I wherein R is CONH$_2$ may be prepared from the corresponding acid I$_1$, employing the procedure as described above for making amide I$_2$ except that ammonium chloride is employed in place of amine E″ to form the amide of the invention I$_3$

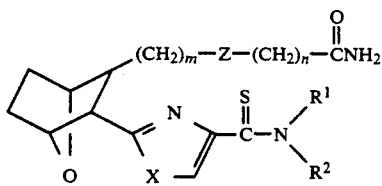

Compounds of formula I wherein R is CH$_2$OH may be prepared from the corresponding ester I$_4$

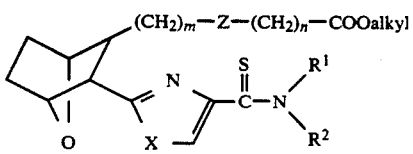

which is treated with a reducing agent such as lithium borohydride (LiBH$_4$) in the presence of diethyl ether and tetrahydrofuran to form the alcohol I$_5$

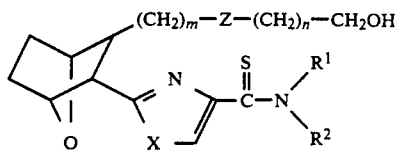

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared by employing starting materials and following the procedures as outlined in U.S. Pat. No. 4,143,054. Examples of such stereoisomers are set out below.

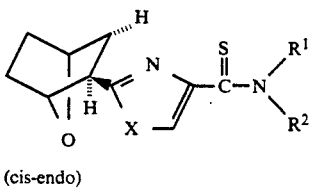

(cis-endo)

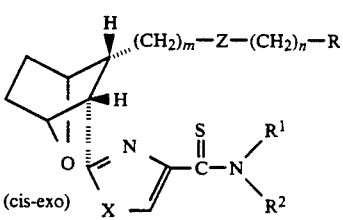

(cis-exo)

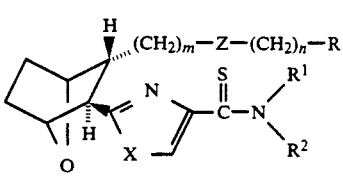

(trans)

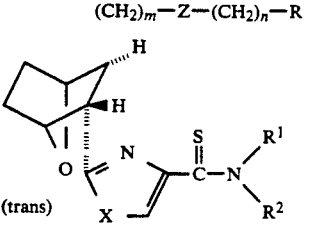

(trans)

The nucleus in each of the compounds of the invention is depicted as

for matter of convenience; it will also be appreciated that the nucleus in the compounds of the invention may be depicted as

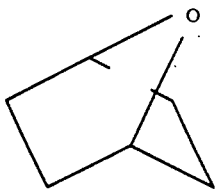

The compounds of this invention are thromboxane receptor antagonists and as such are useful as inhibitors of thromboxane receptor mediated actions. The term "thromboxane receptor antagonist" includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogen-streptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The oxazole derivatives of the invention, that is compounds of formula I where X is O have particularly long duration of action and these may, if desired, be administered in the above dosages once daily, once every other day, or if desired once daily two times a week.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-(1α,2α,3α,4α)]-2-[[3-[4-[[(4-Cyclohexylbutyl)amino]thioxomethyl]-2-oxazolyl]-7-oxabicyclo[2.2.1]hept-2-yl]methyl]benzenepropanoic acid, methyl ester

A. 3-(2-Bromophenyl)-2-propenoic acid, methyl ester

To a stirred solution of 161.2 g (871 mmol) of 2-bromobenzaldehyde in 700 mL of dry THF (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg) eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

TLC (silica gel, 5% EtOAc in hexane—$I_2$):

| | |
|---|---|
| 2-bromobenzaldehyde | 0.29 |
| title compound | 0.20 |

B. 2-Bromobenzenepropanoic acid, methyl ester

A mixture of 201.5 g (836 mmol) of Part A acrylate and 8.4 g of 5% rhodium on alumina catalyst (MCB) in 1.0 L of methanol was stirred at room temperature under an atmosphere of hydrogen (balloon) for in excess of 8 hours. $^1$H NMR analysis of an aliquot showed about a 1:1 mixture of title compound and trans Part A compound with no cis Part A compound. The mixture was diluted with 500 mL additional methanol (MeOH) and 12.6 g more catalyst was added. After hydrogenation overnight the reaction was complete. The reaction mixture was passed through Celite and a Millipore/Fluropore membrane filter (0.5 μm FH) with a prefilter pad, and the filtrate was concentrated in vacuo to obtain two immiscible oils. One of the oils was water soluble and gave a highly acid, i.e. aqueous solution. Solid NaHCO$_3$ and Na$_2$SO$_4$ were carefully added (gas was evolved). The mixture was diluted with CH$_2$Cl$_2$, filtered, and evaporated (and re-evaporated with CH$_2$Cl$_2$ to drive off MeOH) to obtain 196.9 g of clear oil. This oil was 95% pure title compound with 5% of debromo title compound. The corrected yield of title compound was 92% (187.1 g).

TLC (silica gel, 15% EtOAc in hexane—UV):

| | |
|---|---|
| Part A compound | 0.36 |
| (much more strongly UV absorbing) | |
| title compound | 0.40 |

C. 2-Bromobenzenepropanol

To a stirring solution of 196.9 g (95% pure = 187.1 g, 770 mmol) of Part B compound in 770 mL of toluene under argon cooled to 0° (ice bath), was added over 45 minutes 830 mL of 1.0 M diisobutylaluminum hydride (DIBAl-H) in toluene solution (830 mmol, Aldrich). The reaction was not very exothermic. After the mixture was stirred for 1 hour, TLC indicated approximately half of the starting material remained. Next, 580 mL of 1.5 M DIBAl-H in toluene solution (870 mmol, Aldrich) was added slowly. The ice bath was removed and stirring was continued for 2 hours. The mixture was then poured slowly into 1.2 L of 6 M aqueous HCl stirring in an ice bath. This quench was exothermic and gas was evolved. After the mixture was recooled to 0°, the layers were separated, and the organic layer was washed with 1 M aqueous HCl and brine. It was then dried over Na$_2$SO$_4$ and MgSO$_4$ and evaporated (and re-evaporated with CH$_2$Cl$_2$ to drive off toluene) to obtain 173.0 g of clear, colorless oil. This oil was 95% pure title compound with 5% of debromo- title compound. The corrected yield of title compound was 99% (164.3 g).

TLC (silica gel, 15% EtOAc in hexane—anisaldehyde, UV):

| | |
|---|---|
| Part B compound | 0.49 |
| (faintly staining) | |
| Title compound | 0.11 |

D. [3-(2-Bromophenyl)propoxy]dimethyl-(1,1,2-trimethylpropyl)silane

To a stirring solution of 173.0 g (95% pure = 164.3 g, 764 mmol) of Part C compound and 57.8 g of imidazole (850 mmol) in 1.0 L of CHCl$_3$ at room temperature was added slowly 136.6 g (764 mmol) of thexyldimethylchlorosilane. The reaction was mildly exothermic and a precipitate formed. After stirring overnight, $^1$H NMR analysis of an aliquot showed a trace of Part C compound remaining. Additional thexyldimethylchlorosilane (6.8 g, 38 mmol, 0.05 equiv) was added. After 2 days the mixture was evaporated. The residue was diluted with hexane and filtered. The filtrate was evaporated and distilled (150°-180° at 1.2 torr) to obtain 262.8 g of slightly cloudy, colorless oil. This oil was 94% pure title compound with 5% of debromo-title compound. The corrected yield of title compound was 91% (247.0 g).

TLC (silica gel, 15% EtOAc in hexane anisaldehyde):

| | |
|---|---|
| Part C compound | 0.11 |
| Title compound | 0.89 |

E. Bromo[2-[3-[[dimethyl(1,1,2-trimethylpropyl)silyl]oxy]propyl]phenyl]magnesium A 2-L oven-dried flask containing a magnetic stir-bar was charged with 19.0 g of hammer-crushed Mg turnings (782 mmol, Mallinckrodt) and placed under an argon atmosphere. After 440 mL dry THF (distilled from potassium/benzophenone) was added, the Mg was activated at room temperature by introduction of a crystal of iodine and 2 mL of 1,2-dibromoethane (gas was evolved). This was followed by addition of 207.4 g (94% pure = 195.0 g, 546 mmol) of Part D compound in a single portion. The reaction mixture briefly turned colorless, then amber. The exothermic reaction brought the mixture to reflux. Additional dry THF (120 mL) was introduced to ensure product solubility on eventual cooling. Although the reaction was not violently exothermic, foaming made it necessary to cool the mixture with a water bath. The water bath was used intermittently until the exotherm subsided. The mixture was then heated to a gentle reflux for 1 hour and cooled to room temperature. No precipitate formed. The mixture consisted of a brown, clear solution of title compound and some unreacted Mg. This solution was used the same day to prepare title compound F as follows.

F.
[1S-(1α,2α,3α,4α)]-α-[2-[3-[[Dimethyl(1,1,2-trimethylpropyl)silyl]oxy]propyl]phenyl]-7-oxabicyclo[2.2.1]heptane-2,3-dimethanol A 5-L flask containing a magnetic stir-bar was charged with 63.1 g of [3aR-(3aα,4β,7β,7aα)]octahydro-4,7-epoxyisobenzofuran-1-ol (SQ 30,674) (405 mmol) and placed under an argon atmosphere. After 400 mL dry THF (distilled from potassium/benzophenone) was added, SQ 30,674 was dissolved by stirring. The resulting solution was cooled to 0°, and by syringe over 30 minutes, 192 mL of 2.0 M $C_2H_5MgBr$ (Aldrich, prewarmed to 30° to ensure homogeneity, 385 mmol, 0.95 equiv) was added. Gas was evolved. After the addition was complete, stirring at 0° was continued for 1 hour. The solution of previously prepared Part E magnesium compound (546 mmol, 1.35 equiv theoretical) was introduced by cannula over 1 hour. The temperature was maintained at 0° during the addition and for several hours afterward. A small amount of precipitate formed. The mixture was warmed to room temperature, and 50 mL dry THF was added. Some precipitate remained. This mixture was stirred for 6 days before 290 mL of a saturated, aqueous solution of (83 g) $NH_4Cl$ was slowly added. The quench was slightly exothermic, the mixture warming itself to about 40°. The mixture was stirred for 2 hours, and the inorganics formed a white paste. To the mixture was added 1.0 L of $CH_2Cl_2$. The organic supernatant was decanted from the paste. The paste was then stirred with 500 mL $CH_2Cl_2$. The organic layer was decanted, and this procedure was repeated. The combined organic layers were dried over 115 g $Na_2SO_4$ (total volume 3.5 L), and concentrated in vacuo. To drive off THF the residue was re-concentrated after addition of 200 mL $CH_2Cl_2$. This yielded 230 g of an oil. The oil was then quickly dissolved in 2.0 L hexane. Crystallization began in minutes. The mixture was refrigerated with periodic agitation for 5 days. The crystals which formed were filtered (cold) and washed with two 500 mL portions of refrigerated hexane. After exposure to vacuum, 145.9 g of crystals (mp 99.5°-100.5°) were obtained. The crystals, pure, and a single diastereomer of Part F compound, represented an 83% yield. The mother liquors were evaporated, redissolved in 200 mL hexane, and placed in the freezer for 30 days. A second crop of crystals (8.7 g, pure, single diastereomer of Part F compound, 5% additional yield) was collected as above. (In an earlier run, yields of the cospotting major and minor diastereomers were 94% and 5% respectively. The minor diastereomer is an oil).

TLC (silica gel, 100% EtOAc—anisaldehyde):

| SQ 30,674 | 0.35 |
| Part F compound | 0.78 |

$^{13}C$ NMR (67.8 MHz in $CDCl_3$) 141.8, 138.7, 129.5, 127.3, 126.2, 125.5, 79.5, 77.3, 67.4, 62.2, 61.7, 51.7, 49.0, 34.2, 34.1, 29.7, 29.7, 28.0, 25.2, 20.3, 18.5, −3.3.

G.
[1S-(1α,2α,3α,4α)]-2-[[2-[3-[[Dimethyl(1,1,2-trimethylpropyl)silyl]oxy]propyl]phenyl]methyl]-7-oxabicyclo[2.2.1]heptane-3-methanol A mixture of 143.0 g (329 mmol) of Part F compound and 28.6 g of 20% palladium hydroxide on carbon catalyst (moist, <50% water, Aldrich) in 2.0 L of glacial acetic acid was stirred rapidly under an atmosphere of hydrogen (balloon) at room temperature for 30 hours. The reaction mixture was filtered through filter paper to remove most of the catalyst. The filtrate was evaporated to 500 mL on a rotovapor in a 30° water bath under high vacuum. This was then passed through a Millipore/Fluropore membrane filter (0.5 μm FH) with a prefilter pad. Evaporation as above was followed by azeotropic removal of acetic acid (AcOH) with toluene (500 mL three times) and re-evaporation with $CH_2Cl_2$ to drive off toluene. The crude product, 144.9 g of an oil, consisted largely of title compound (approximately 90%) with small amounts of solvent, the acetate of title compound (identical with Part H compound, less than 5%), and desilylated title compound (diol, less than 5%).

TLC (silica gel, 25% EtOAc in hexane—anisaldehyde):

| Part F compound | 0.07 |
| Title compound | 0.16 |
| Part H compound | 0.50 |
| desilylated title compound (diol) | 0.00 |

TLC (silica gel, 100% EtOAc—anisaldehyde):

| Part F compound | 0.82 |
| Title compound | 0.85 |
| Part G compound | 0.93 |
| desilylated G (diol) | 0.20 |

H.
[1S-(1α,2α,3α,4α)]-2-[[2-[3-[[Dimethyl(1,1,2-trimethylpropyl)silyl]oxy]propyl]phenyl]methyl-7-oxabicyclo[2.2.1]hept-2-yl]heptane-3-methanol, acetate ester A solution of 144.9 g (<329 mmol) of crude Part G compound in 200 mL pyridine (Burdick & Jackson) was stirred magnetically under argon at room temperature while 50 mL (54 g, 530 mmol) of acetic anhydride was added in a single portion. The reaction mixture warmed to a peak temperature of about 41° after 30 minutes. After 16 hours the homogeneous mixture was rotoevaporated using a 70° water bath. The residue was coevaporated three times with toluene (500 mL). This gave 163.5 g of an oil, crude title compound. The crude product contained toluene, but no residual pyridine.

TLC (silica gel, 25% EtOAc in hexane—anisaldehyde):

| Part G compound | 0.20 |
| Part H compound | 0.54 |

13C NMR (67.8 MHz in CDCl3) 170.9, 140.4, 138.7, 129.6, 129.4, 126.2, 125.9, 79.3, 79.2, 63.8, 62.4, 46.9, 46.0, 34.2, 34.0, 30.6, 29.5, 29.5, 28.9, 25.1, 21.0, 20.4, 18.5, −3.4.

I.
[1S-(1α,2α,3α,4α)]-2-[[3-[(Acetyloxy)methyl)]-7-oxabicyclo[2.2.1]hept-2-yl]methyl]benzenepropanoic acid To a stirring solution of 163.5 g of crude Part H compound in 2.0 L acetone in a room temperature bath, was added slowly (over about 1 hour in 50 mL portions) 240 mL of Jones' Reagent with Mn+2. Exothermic reaction brought the mixture to near reflux. As precipitate formed stirring became very difficult. The red color of the reagent persisted after the last portion was introduced. The excess reagent was quenched 30 minutes later by addition of 50 mL 2-propanol. The precipitated Cr salts were easily filtered. The salts were washed with acetone. The filtrate (2.4 L) was evaporated, and two immiscible oils were obtained. After addition of 500 mL CH2Cl2, 100 mL brine, and 300 mL water, separation of the organic and aqueous layers was difficult. Introduction of 300 mL CHCl3 allowed good separation. The aqueous layer was re-extracted twice with 300 mL CHCl3, and the combined extracts were dried over NaSO4 and evaporated in vacuo. This provided 164.5 g of crude title compound (containing desilylation by-product), a clear oil.

TLC [silica gel, 50% (5% CH3COOH in ethyl acetate (EtOAc)) in hexane—anisaldehyde]:

| Part H compound | 0.89 |
|---|---|
| Title compound | 0.42 |

J.
[1S-(1α,2α,3α,4α)]-2-[[3-(Hydroxymethyl)7-oxabicyclo[2.2.1]hept-2-yl]methyl]benzenepropanoic acid, methyl ester A solution of 164.5 g of crude Part I compound in 1.0 L of acidic methanol (prepared by cautious addition of 10 mL of acetyl chloride to 1.0 L of methanol) was stirred under argon in a 2-L flask. TLC indicated that the reaction proceeded predominantly through one distinct intermediate. After 16 hours 30 g of NaHCO3 was added cautiously over 10 minutes. Neutralization was not exothermic, but gas was evolved. The mixture was stirred for 30 minutes before it was cautiously evaporated. The residue was diluted with 500 mL CH2Cl2, dried over Na2SO4, and filtered. After the filtrate was evaporated, the crude product was coevaporated in vacuo twice with toluene (60° bath, to remove some of the desilylation by-product). This gave 119.3 g of an oil. Crude title compound was judged to be roughly 75% pure with only about a third of an equivalent of desilylation by-product and a little diol (Part G by-product).

TLC (silica gel, 50% (5% CH3COOH in EtOAc) in hexane—anisaldehyde):

| Part I compound | 0.35 |
|---|---|
| intermediate | 0.53 |
| title compound | 0.31 |
| diol | 0.11 |

K.
[1S-(1α,2α,3α,4α)]-2-[(3-Carboxy-7-oxabicyclo[2.2.1]hept-2-yl)methyl]benzenepropanoic acid, methyl ester To a stirring solution of 93.6 g (78% of the sample) of crude Part J compound in 1.5 L acetone in a room temperature bath, was added slowly (over about 1 hour in 50 mL portions) 150 mL of Jones' Reagent with Mn+2. (Jones' Reagent was prepared as described in Fieser & Fieser, "Reagents for Organic Synthesis", vol. 1, p. 142—Djerassi procedure. Into this Jones' Reagent was dissolved 1.0 g MnSO4.H2O per L.). Exothermic reaction brought the mixture to near reflux. As precipitate formed stirring became very difficult. The red color of the reagent persisted after the last portion was introduced. The excess reagent was quenched 30 minutes later by addition of 50 mL 2-propanol. The precipitated Cr salts were easily filtered. The salts were washed with acetone. The filtrate was evaporated, and two immiscible oils were obtained. After addition of 500 mL CHCl3, 100 mL brine, and 300 mL water, separation of the organic and aqueous layers was uncomplicated. The aqueous layer was re-extracted twice with 250 mL CHCl3, and the combined extracts were dried over Na2SO4 and evaporated. This provided 109.6 g of crude title acid, a pale green, clear oil. A portion (30.6 g, 28% of the sample) of the crude title acid was flash chromatographed (1.0 kg Merck silica gel, 40% to 100% (5%CH3COOH in EtOAc) in hexane gradient). This provided 18.2 g of pure title acid as a viscous oil. Also isolated was 1.4 g of the diacid corresponding to title acid, a solid. The overall yields from Part F compound were 80% and 6%, respectively.

TLC (silica gel, 50% (5% CH3COOH in EtOAc) in Hexane—anisaldehyde):

| Part J compound | 0.33 |
|---|---|
| diol | 0.12 |
| title acid | 0.31 |
| diacid | 0.13 |

L. N-(Cyclohexylbutyl)-L-serinamide

To a solution of 14.3 g of 4-cyclohexylbutylamine hydrochloride (74.7 mmol), 16.1 g t-butoxycarbonyl (BOC)-(L)-serine (78.4 mmol, 1.05 equiv), 10.1 g 1-hydroxybenzotriazole hydrate (74.7 mmol, 1.00 equiv), and 7.9 g N-methylmorpholine (78.4 mmol, 1.05 equiv) in 200 mL N,N-dimethyl formamide (DMF) (Burdick & Jackson) stirring under argon at 0°, was added 15.0 g WSC (78.4 mmol, 1.05 equiv) in a single portion. All of the WSC dissolved. The reaction mixture was allowed to slowly warm to room temperature overnight, and a precipitate formed. The mixture was rotoevaporated (60° bath) to 90 g of oil plus solid. This was diluted with 400 mL EtOAc and washed with 200 mL 0.3 M aqueous HCl twice (all solids dissolved at this point), then 200 mL 1.0 M aqueous NaHCO3 twice. To the organic layer was added 500 mL toluene, and this was dried over Na2SO4 and evaporated. After coevaporation with toluene, 28.4 g of a thick solidifying oil was obtained. This material, BOC-title compound, was dissolved in 150 mL CH2Cl2, and while stirring at room temperature under argon, 100 mL trifluoroacetic acid was added (gas was evolved). After 4 hours the solvent was evaporated, and after coevaporation with CHCl3, the crude product was flash chromatographed (1.0 kg silica gel, 10% (10% conc. aq. NH₃ in CH₃OH) in CH₂Cl₂) to obtain 13.4 g of 95% pure title compound as a white solid. The corrected yield of title compound was 70% (12.7 g) overall from 4-cyclohexylbutylamine hydrochloride.

TLC (silica gel, 10% (10% conc. aq. NH₃ in CH₃OH) in CH₂Cl₂—anisaldehyde):

| 4-Cyclohexylbutylamine | 0.27 |
|---|---|
| BOC-title compound | 0.43 |
| title compound | 0.17 |

M.
[1S-(1α,2α,3α(R*),4α)]-2-[[3-[[[2-[(4-Cyclohexylbutyl)amino]-1-(hydroxymethyl)-2-oxoethyl]amino]carbonyl]-7-oxabicyclo[2.2.1]hept-2-yl]methyl]benzenepropanoic acid, methyl ester To a stirred solution of 16.7 g of Part K compound (52.5 mmol), 13.4 g of Part L compound (95% pure=12.7 g, 52.5 mmol), 7.8 g of 1-hydroxybenzenetriazole monohydrate (57.8 mmol, 1.10 equiv), and 5.8 g of N-methylmorpholine (57.8 mmol, 1.10 equiv) in 250 mL of DMF (Burdick & Jackson) under argon at 0°, was added 11.1 g of WSC (57.8 mmol, 1.10 equiv). The WSC dissolved completely. The mixture was allowed to warm to room temperature overnight. No precipitate formed. The mixture was rotoevaporated (60° bath). The residue was diluted with 700 mL EtOAc—solids did not all dissolve—and washed with 250 mL 0.3 M aqueous HCl, then 250 mL 1.0 M aqueous NaHCO₃. The still undissolved solid was desired product according to TLC. Addition of 200 mL CH₂Cl₂ did not give a solution. This was washed with 150 mL 0.3 M aqueous HCl plus 50 mL brine, then 250 mL 1.0 M aqueous NaHCO₃. After addition of 500 mL more CH₂Cl₂ a solution formed. This was dried over Na₂SO₄ and evaporated in vacuo. Crude title compound, 30.7 g of white solid, was obtained. This material was about 93% pure. The corrected yield (28.5 g) of title compound (a single diastereomer) was 100%.

TLC (silica gel, 10% (10% conc. aq. NH₃ in CH₃OH) in CH₂Cl₂—anisaldehyde):

| Part K compound | 0.42 |
|---|---|
| Part L compound | 0.25 |
| Title compound | 0.48 |

TLC (silica gel, 50% (5% CH₃COOH in EtOAc) in hexane—anisaldehyde):

| Part K compound | 0.34 |
|---|---|
| Part L compound | 0.00 |
| Title compound | 0.12 |

N.
[1S-(1α,2α,3α,4α)]-2-[[3-[4-[[(4-Cyclohexylbutyl)amino]carbonyl]-4,5-dihydro-2-oxazolyl]-7-oxabicyclo[2.2.1]hept-2-yl]methyl]benzenepropanoic acid, methyl ester A stirred solution of 30.7 g of crude Part M compound (93% pure=28.5 g, 52.5 mmol) in 800 mL of dry CH₂Cl₂ under argon at room temperature was cooled to 0°. As the starting material began to precipitate, 12.1 g of (C₂H₅)₃N (120 mmol), then 6.9 g of methanesulfonyl chloride (60 mmol) were added. The precipitate redissolved. After 40 minutes the mixture was warmed to room temperature, and 30 minutes later it was evaporated. To the residue (crude mesylate of Part M compound) under argon, was added 1.0 L of acetone and 27.6 g K₂CO₃ (200 mmol). The mixture was refluxed for 2 hours and refrigerated overnight. The solid was filtered off and rinsed with acetone. TLC indicated that the solid contained product even after extensive rinsing. After further rinsing with CH₂Cl₂, almost all of product was extracted. The filtrate was evaporated and flash chromatographed (500 g silica gel, 20% acetone in toluene) to obtain 24.9 g of a solid. ¹H NMR indicated either pure title compound as an unequal mixture of two diastereomers (90% yield) or one diastereomer of title compound plus an impurity.

TLC (silica gel, 20% acetone in toluene—anisaldehyde):

| Part M compound | 0.13 |
|---|---|
| mesylate of Part M compound | 0.21 |
| title compound | 0.34 |

O.
[1S-(1α,2α,3α,4α)]-2-[[3-[4-[[(4-Cyclohexylbutyl)amino]carbonyl]-2-oxazolyl]7-oxabicyclo[2.2.1]hept-2-yl]methyl]benzenepropanoic acid, methyl ester To a stirred suspension of 22.3 g (100 mmol) of cupric bromide in 250 mL of EtOAc (Burdick & Jackson) at room temperature under argon, was added 30.4 g (200 mmol) of 1,8-diazabicyclo[5.4.0]undec-7-ene (DBU). The resulting dark mixture was stirred for 15 minutes before a solution of 24.9 g of Part N compound (if pure, 47.5 mmol) in 250 mL of CHCl₃ (Burdick & Jackson) was added. The mixture warmed to about 45° (simply due to the heat of mixing of the two solvents). After 18 hours 22.3 g cupric bromide and 15.2 g DBU were added. After another 25 hours (TLC showed almost complete reaction), 11.2 g cupric bromide and 7.6 g DBU were added. After 4 hours more, the reaction mixture was poured into a 6-L separatory funnel. A residual heavy syrup was transferred by dissolving with CH₂Cl₂. This was shaken with 1.0 L of EtOAc and 1.4 L of a 1:1 (vol:vol) mixture of saturated aqueous NH₄Cl and concentrated aqueous ammonia. Separation was poor. Addition of 750 mL diethyl ether (Et₂O) allowed good separation. Two further extractions of the aqueous layer with 800 mL EtOAc proceeded smoothly. The extracts were dried over Na₂SO₄ and evaporated. Flash chromatography (750 g silica gel, 25% to 40% EtOAc in hexane gradient) allowed isolation of 16.5 g of pure title compound as a white solid. The yield of title compound was 67% assuming pure Part N compound. Also isolated was 1.8 g (6% yield) of bromo-title compound (brominated at the 5 position of the oxazole ring) as a gum.

TLC (silica gel, 20% acetone in toluene—anisaldehyde):

| Part N compound | 0.31 |
|---|---|
| title compound | 0.47 |
| bromo-title compound | 0.61 |

P.
[1S-(1α,2α,3α,4α)]-2-[[3-[4-[[(4-Cyclohexylbutyl-)aminothioxomethyl]-2-oxazolyl]7 TM oxabicyclo[2.2.-1hept-2-yl]methyl]benzenepropanoic acid, methyl ester To a solution of 410 mg 0.74 mmol) of Part O amide and 70 μL (0.87 mmol, Burdick and Jackson) of pyridine in 25 mL of dry methylene chloride (distilled from phosphorous pentoxide) was added 685 mg (1.54 mmol, Aldrich) of phosphorous pentasulfide and the mixture was heated to reflux for 16 hours. The reaction mixture was cooled and filtered through a pad of Celite. The filtrate was partitioned between 20 mL of methylene chloride and 20 mL of aqueous NaOH solution. The organic layer was separated, dried (magnesium sulfate) and concentrated in vacuo to give an oil. The crude material was purified by flash chromatography (Merck silica, 15×3.0 cm, 1:3 ethyl acetate/hexane) to afford 344 mg (0.62 mmol, 84%) of title thioamide as a yellow glass.

EXAMPLE 2

[1S-(1α,2α,3α,4α)]-2-[[3-[4-[[(4-Cyclohexylbutyl-)amino]thioxomethyl]-2-oxazolyl]-7-oxabicyclo[2.2.1-]hept-2-yl]methyl]benzenepropanoic acid A solution of 340 mg (0.62 mmol) of Example 1 ester and 100 mg (2.38 mmol, Aldrich) of lithium hydroxide monohydrate in 7.5 mL of 2:1 THF/water was stirred rapidly at room temperature for 6 hours. The reaction was acidified by addition of 2.6 mL of 1M aqueous HCl solution, then partitioned between 20 mL of ethyl acetate and 20 mL of water. The aqueous layer was separated and extracted with an additional 20 mL of ethyl acetate. The organic extracts were combined, dried (magnesium sulfate) and concentrated in vacuo to give a solid. The crude solid was recrystallized (ethyl acetate/hexane) to afford 286 mg (0.55 mmol, 88%) of title acid as a pale yellow solid, mp 135°-137° C.

IR(KBr): 3276, 2923, 2850, 1709, 1591, 1522, 1448, 1397, 1307 cm$^{-1}$.

MS(CI): 525 (M+H)+.

OR: [α]$_D$= +25° (c=0.25 in chloroform).

TLC: R$_f$ (silica gel, 1:9 methanol/methylene chloride)=0.56, ammonium molybdate/ceric sulfate and UV, homogeneous.

Analysis Calc'd for C$_{30}$H$_{40}$N$_2$O$_4$S: C, 68.67; H, 7.68; N, 5.34; S, 6.11; Found: C, 68.86; H, 7.78; N, 5.33; S, 5.98.

EXAMPLE 3

[1S-(1α,2α,3α,4α)]-2-[[3-[4-[[[4-(4-Chlorophenyl)butyl-]amino]thioxomethyl]-2-oxazolyl]-7-oxabicyclo[2.2.1-]hept-2-yl]methyl]benzenepropanoic acid A. 1-Bromo-2-[3-[[Dimethyl(1,1,2-trimethylpropyl)-silyl]oxy]propyl]benzene To a solution of 29.0 g (135 mmol) of crude Example 1 Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine then 200 mg (1.64 mmol, Aldrich) of 4-dimethylaminopyridine. The reaction mixture was stirred at room temperature for 18 hours. The resulting slurry was diluted with 100 mL of hexane, cooled to 0° with stirring for 15 minutes then filtered to remove solid triethylamine hydrochloride. The filtrate was concentrated in vacuo to give an oil.

The crude oil was purified by flash chromatography (Merck silica, 15×10 cm, 1:9 ethyl acetate/petroleum ether) to afford 45.5 g (127 mmol, 94%) of title compound as a colorless liquid.

B.
[1S-(1α,2α,3α,4α)]-[2-[3-[[Dimethyl(1,1,2-trimethylpropyl)silyl]oxy]propyl]phenyl]-7-oxabicyclo[2.2.1-]heptane-2,3-dimethanol To a solution of 5.00 g (14.0 mmol) of Part A compound in 30 mL of dry diethyl ether (distilled from ketyl) cooled to −100° was added dropwise 15 mL (1.7M in pentane, 25 mmol, Aldrich) of t-butyllithium solution over 15 minutes. The reaction mixture was stirred at −100° for 15 minutes then at 0° for 15 minutes. The resulting pale yellow anion solution was re-cooled to −78° then 30 mL of dry THF (distilled from ketyl) was introduced followed by the rapid addition of a solution of 875 mg (5.61 mmol) of [3aR-(3aα,4β,7β,-7aα)]-octahydro-4,7-epoxyisobenzofuran-1-ol in 10 mL of THF. The reaction mixture was warmed to 0°, stirred for 1 hour, quenched with 5 mL of water then partitioned between 100 mL of water and 25 mL of ethyl acetate. The organic layer was separated and the aqueous layer was extracted with an additional 25 mL of ethyl acetate. The organic extracts were combined, dried (magnesium sulfate) and concentrated in vacuo to give an oil. The crude oil was purified by flash chromatography (Merck silica, 12×5.0 cm, 1:4 ethyl acetate/petroleum ether then 4:1 ethyl acetate/petroleum ether) to afford 2.35 g (5.41 mmol, 97%) of title diasteromeric alcohols as a colorless oil.

C. [1S-(1α,2α,3α,4α)]-2-[[2-[3-[[Dimethyl(1,1,2-trimethylpropyl)silyl]oxy]propyl]phenyl]methyl]-7-oxabicyclo[2.2.1]heptane-3-methanol A mixture of 1.90 g (4.38 mmol) of Part B diastereomeric alcohols and 1.9 g of 20% palladium hydroxide on carbon catalyst (moist, <50% water, Aldrich) in 60 mL of glacial acetic acid was stirred rapidly under an atmosphere of hydrogen (balloon) for 5 hours. The reaction mixture was filtered through a 4 μM polycarbonate membrane and the filtrate was concentrated in vacuo (room temperature bath). The residue was partitioned between 50 mL of water and 50 mL of ethyl acetate. The organic layer was separated, washed with 50 mL of 1M aqueous sodium hydroxide solution, dried (magnesium sulfate) and concentrated in vacuo to give an oil. The crude material was purified by flash chromatography (Merck silica, 12×5.0 cm, 1:2 ethyl acetate/petroleum ether) to afford 1.03 g (2.39 mmol, 55%) of title compound as a colorless oil. In addition, 573 mg (1.37 mmol, 30%) of Part C starting material (as a single diastereomer) was recovered.

D.
[1S-(1α,2α,3α,4α)]-2-[[3-(Hydroxymethyl)-7-oxabicyclo[2.2.1]hept-2-yl]methyl]benzenepropanoic acid, methyl ester A solution of 1.00 g (2.39 mmol) of Part C compound and 50 mg (0.41 mmol, Aldrich) of 4-dimethylaminopyridine in 6 mL of 1:1 dry pyridine/acetic anhydride was stirred at room temperature for 2 hours. The reaction mixture was concentrated in vacuo and the residue partitioned between 25 mL of ethyl acetate and 20 mL 1M aqueous HCl solution. The organic layer was separated, washed with 20 mL of 1M aqueous NaOH then 20 mL of brine, dried (magnesium sulfate) and concentrated in vacuo to afford the crude acetate as an oil.

To a solution of the crude acetate in 15 mL of reagent acetone cooled to 0° was added rapidly 3.3 mL (2.6M in $Cr^{+6}$, for preparation see Fieser & Fieser, "Reagents for Organic Synthesis," Vol. 1, p. 142) of Jones reagent. The reaction mixture was stirred for 2 hours, quenched by addition of 1 mL of isopropanol and stirred for an additional 30 minutes. The resulting green slurry was filtered through a pad of Celite. The filtrate was concentrated in vacuo and the residue partitioned between 25 mL of diethyl ether and 25 mL of water. The organic layer was separated and concentrated in vacuo to give the crude acetate-acid as an oil.

A solution of the crude acetate-acid in 15 mL of 2:1 1M aqueous NaOH/THF was stirred at room temperature for 30 minutes. The reaction mixture was cooled in an ice-bath, quenched by addition of 15 mL of 1M aqueous HCl solution then extracted with two-25 mL portions of diethyl ether. The ether extracts were combined, washed with 25 mL of brine and concentrated in vacuo to give the crude alcohol-acid as an oil.

A solution of the crude alcohol-acid in 10 mL of acidic methanol (prepared by addition of 0.5 mL of acetyl chloride to 10 mL of dry methanol at 0°) was stirred at 0° for 2 hours then concentrated in vacuo. The resulting oil was purified by flash chromatography (Merck silica, 15×3.0 cm, ethyl acetate) to afford 526 mg (1.76 mmol, 74% from Part C compound) of title compound as a colorless oil.

E.

[1S-(1α,2α,3α,4α)]-2-[[3-Carboxy-7-oxabicyclo[2.2.1]hept-2-yl]methyl]benzenepropanoic acid, methyl ester To a solution of 495 mg (1.63 mmol) of Part D compound in 5 mL of reagent acetone cooled to 0° was added rapidly 2.0 mL (2.6M in $Cr^{+6}$) of Jones reagent. The reaction mixture was warmed to room temperature, stirred for 2 hours then quenched by addition of ~1 mL of isopropanol. After 15 minutes the resulting green slurry was filtered through a pad of Celite. The filtrate was partitioned between 20 mL of diethyl ether and 20 mL of water. The organic layer was separated and the aqueous layer was extracted with an additional 20 mL of diethyl ether. The ether extracts were combined, dried (magnesium sulfate) and concentrated in vacuo to give 560 mg (1.59 mmol, 98%) of crude title compound as a colorless oil.

F.

[1S-(1α,2α,3α,4α)]-2-[[3-[[1-(Hydroxymethyl)-2-oxo-2-(phenylmethoxy)ethyl]amino]carbonyl]-7-oxabicyclo[2.2.1]hept-2-yl]methyl]benzenepropanoic acid, methyl ester To a solution of 490 mg (1.54 mmol) of Part E acid in 10 mL of dry THF (distilled from ketyl) cooled to 0° was added 392 mg (1.69 mmol, Sigma) of L-serine benzyl ester hydrochloride, 228 mg (1.69 mmol, Aldrich) of 1-hydroxybenzotriazole hydrate and 530 μL (3.8 mmol, distilled from calcium hydride) of triethylamine. The mixture was stirred for 5 minutes then 348 mg (1.69 mmol, Aldrich) of dicyclohexylcarbodiimide was added in one portion. The reaction was stirred at 0° for 3 hours then warmed to room temperature for 16 hours. The resulting slurry was diluted with 10 mL of ethyl acetate, cooled to 0° for 15 minutes then filtered. The filtrate was concentrated in vacuo to give an oil. The crude material was purified by flash chromatography (Merck silica, 15×3.0 cm, ethyl acetate) to afford 540 mg (1.09 mmol, 71%) of title compound as a white solid.

G.

[1S-(1α,2α,3α,4α)]-2-[[3-[4,5-Dihydro-4-[(phenylmethoxy)carbonyl]-2-oxazolyl]-7-oxabicyclo[2.2.1]hept-2-yl]-methyl]benzenepropanoic acid, methyl ester To a solution of 525 mg (1.06 mmol) of Part F compound, 843 mg (3.10 mmol, Aldrich) of triphenylphosphine and 540 μL (3.1 mmol, Aldrich) of diisopropylethylamine in 6 mL of 5:1 dry acetonitrile/methylene chloride was added at room temperature 300 μL (3.1 mmol, Mallinckrodt) of reagent carbon tetrachloride. The reaction mixture was stirred for 2 hours then diluted with 15 mL of ethyl acetate followed by the slow addition of 15 mL of saturated aqueous sodium bicarbonate solution. The resulting mixture was stirred for 5 minutes then partitioned between 20 mL of ethyl acetate and 20 mL of water. The organic layer was separated, washed with 20 mL of brine, dried (sodium sulfate) and concentrated in vacuo to give a yellow oily solid. The crude material was purified by flash chromatography (Merck silica, 20×3.0 cm, 2:1 ethyl acetate/petroleum ether) to afford 380 mg (0.80 mmol, 75%) of title oxazoline as a pale yellow solid.

H.

[1S-(1α,2α,3α,4α)]-2-[[3-[4-[(Phenylmethoxy)carbonyl]-2-oxazolyl]-7-oxabicyclo[2.2.1]hept-2-yl]methyl]benzenepropanoic acid, methyl ester To a solution of 375 mg (0.79 mmol) of Part G oxazoline in 10 mL of dry methylene chloride (distilled from phosphorous pentoxide) was added 750 mg of Example 1, Part J, nickel peroxide oxidant (K. Nakagawa et al, J. Org. Chem. 27, 1597 (62)) at room temperature. The reaction mixture was stirred for 1 hour then an additional 190 mg of oxidant was added. After 30 minutes the reaction mixture was diluted with 20 mL of ethyl acetate followed by the addition of 10 mL of 3M aqueous sodium bisulfite solution. The resulting mixture was stirred rapidly for 20 minutes then 10 mL of water was added. The organic layer was separated and the aqueous layer extracted with an additional 20 mL of ethyl acetate. The organic extracts were combined, washed with 25 mL of 1M aqueous sodium citrate solution, dried (magnesium sulfate) and concentrated in vacuo to give an oil. The crude material was purified by flash chromatography (Merck silica, 15×5.0 cm, 2:3 ethyl acetate/petroleum ether) to afford 180 mg (0.38 mmol, 48%) of title oxazole as an oil.

I. 4-(4-Chlorophenyl)butylamine (a) 3-(4-Chlorpenyl)propanol

To a stirred solution of 5.0 g (27 mmol) of 3-(4-chlorophenyl)propionic acid in 30 ml of tetrahydrofuran at 0° C., 30 ml (1M in THF, 30 mmol) of borane-tetrahydrofuran solution was added dropwise. The reaction was stirred for 15 hours. The reaction mixture was concentrated in vacuo. The residue was quenched with water and partitioned between diethyl ether and saturated sodium bicarbonate. The organic layer was separated and the aqueous layer was extracted twice with 40 ml of diethyl ether. The organic layers were combined and washed with brine, dried over $MgSO_4$ and concentrated in vacuo to obtain 3.9 g of a colorless oil.

$^{13}$C NMR (CDCl$_3$, 67.8 MHz)δ: 140.0, 131.0, 129.9, 129.0, 161.0, 132.5, 131.0.

(b) 3-(4-Chlorophenyl)propyl bromide

To a stirred solution of 4.15 g (15.8 mmol) of triphenylphosphine in 100 ml of toluene at 0° C., 1.51 ml (15.8 mmol) of bromine was added dropwise. This mixture was stirred for 3 hours then a solution of 3.90 g (22.9 mmol) of Part (a) alcohol and 1.63 ml (15.8 mmol) of pyridine in 20 ml of toluene was added. A solution of 25 ml hexane and 25 ml diethyl ether was added, and a brown mass was formed. The liquid was decanted and concentrated in vacuo. The residue was triturated with hexane:ethyl acetate and triphenylphosphine oxide was precipitated. The solid was filtered and the filtrate was concentrated in vacuo to give a yellow oil. The oil was purified by flash chromatography to obtain 1.80 g (7.72 mmol, 49%) of the desired product.

$^{13}$C NMR (CDCl$_3$)δ: 138.7, 131.6, 129.6, 128.3, 33.7, 33.0, 32.5.

(c) 4-(4-Chlorophenyl)butyronitrile

To a solution of 3.10 g (13.3 mmol) of Part (b) bromide in 36 ml of ethanol stirred under argon at room temperature, was added a solution of 4.26 g (65.4 mmol) of potassium cyanide in 12 ml of water. The reaction was incomplete after 5 hours as indicated by TLC. To the reaction mixture 4 ml of THF and 4 ml of water were added, and a homogeneous reaction mixture was obtained. After stirring for 12 hours, water and diethyl ether were added. The organic layer was separated. The aqueous layer was extracted twice with 50 ml of diethyl ether. The organic layers were combined, washed with water, brine, dried over MgSO$_4$ and concentrated in vacuo to give an oil. The oil was purified by flash chromatography (Merck silica gel 90:10 hexane:ethyl acetate) to obtain 1.80 g (10.1 mmol, 76%) of title nitrile as a clear oil.

$^{13}$C NMR (CDCl$_3$)δ: 138.0, 132.1, 129.6, 128.6, 33.5, 26.6, 16.2

(d) 4-(4-Chlorophenyl)butylamine

To a solution of 1.80 g (10 mmol) of Part (c) nitrile in 70 ml of diethyl ether stirred under argon at 0° C., was added 0.38 g (10 mmol) of lithium aluminum hydride. Gas was evolved. After 20 minutes, the reaction mixture was quenched with 0.4 ml of water, then 0.4 ml of 1N NaOH, then 1.2 ml water, stirring for a few minutes after each addition. The resulting white precipitate was filtered and the filtrate was concentrated in vacuo to obtain 1.5 g (8.20 mmol, 82%) of title amine as a clear oil.

$^{13}$C NMR (CDCl$_3$)δ: 140.7, 131.2, 129.5, 128.2, 41.8, 34.9, 33.0, 28.4

J.
[1S-(1α,2α,3α,4α)]-2-[[3-[4-[[[4-(4-Chlorophenyl)butyl]amino]carbonyl]-2-oxazolyl]-7-oxabicyclo[2.2.1]hept-2-yl]methyl]benzenepropanoic acid, methyl ester A mixture of 175 mg (0.37 mmol) of Part H oxazole and 30 mg of 20% palladium hydroxide on carbon catalyst (moist, <50% water, Aldrich) in 5 mL of reagent ethyl acetate was stirred under an atmosphere of hydrogen (balloon) for 1 hour. The catalyst was removed by filtration through a 0.4 μM polycarbonate membrane. The filtrate was concentrated in vacuo to afford 141 mg (0.37 mmol, 100%) of the crude acid ([1S-(1α,2α,3α,-4α)]-2-[[3-[4-[carboxy]-2-oxazolyl]-7-oxabicyclo[2.2.1-]hept-2-yl]methyl]benzenepropanoic acid, methyl ester) as a white solid, mp 156°–158°.

To a solution of 135 mg (0.35 mmol) of the crude acid in 3 mL of dry methylene chloride (distilled from phosphorous pentoxide) was added at room temperature a small drop of DMF then 40 μL (0.46 mmol, Aldrich) of oxalyl chloride. The reaction mixture was stirred for 30 minutes then concentrated in vacuo to give the crude acid chloride as a yellow solid. The acid chloride was solubilized in 3 mL of dry methylene chloride then cooled to 0° and a solution of 84 mg (0.46 mmol) of Part I amine and 70 μL (0.50 mmol, distilled from calcium hydride) of triethylamine in 1 mL of dry methylene chloride was added rapidly. The reaction mixture was stirred for 30 minutes then partitioned between 25 mL of ethyl acetate and 15 mL of 1M aqueous HCl solution. The organic layer was separated and the aqueous layer was extracted with an additional 10 mL of ethyl acetate. The organic extracts were combined, dried (magnesium sulfate) and concentrated in vacuo to give a yellow solid. The crude material was purified by flash chromatography (Merck silica, 18×1.5 cm, 3:1 ethyl acetate/petroleum ether) to afford 161 mg (0.29 mmol, 83%) of title compound as a white solid, mp 140°–142°.

K.
[1S-(1α,2α,3α,4α)]-2-[[3-[4-[[[4-(4-Chlorophenyl)butylamino]thioxomethyl]-2oxazolyl]-7-oxabicyclo[2.2.1]hept-2-yl]methyl]benzenepropanoic acid, methyl ester Following the procedure of Example 1 Part P except substituting the Example 2 Part J amide for the Example 1 Part 0 amide, the title ester is obtained.

EXAMPLE 4

[1S-(1α,2α,3α,4α)]-2-[[3-[4-[[[4-(4-Chlorophenyl)butyl)amino]thioxomethyl-2-oxazolyl]-7-oxabicyclo[2.2.1-]hept-2-yl]methyl]benzenepropanoic acid Following the procedure of Example 2 except substituting the Example 3 ester for the Example 1 ester, the title compound is obtained.

EXAMPLE 5

[1S-(1α,2α,3α,4α)]-2-[[3-[4-[(Pentylamino)thioxomethyl]-2-oxazolyl]-7-oxabicyclo[2.2.1]hept-2-yl]methyl]-benzenepropanoic acid, methyl ester A.
[1S-(1α,2α,3α,4α)]-2-[[3-4-[(Pentylamino)carbonyl]-2-oxazolyl]-7-oxabicyclo[2.2.1]hept-2-yl]methyl]benzenepropanoic acid, methyl ester To a solution of 200 mg (0.52 mMol) of oxazole acid intermediate prepared in Example 3, Part J in 3 mL of dry methylene chloride (distilled from phosphorous pentoxide) was added a small drop of dimethylformamide then 55 μL (0.63 mMol, Aldrich) of oxalyl chloride. The reaction mixture was stirred until gas evolution ceased, about 15 minutes, then concentrated in vacuo to give a solid. The solid was dissolved in 2 mL of sieve-dried benzene (Burdick and Jackson) then concentrated in vacuo to give the crude acid chloride as a solid. The crude acid chloride was dissolved in 5 mL of dry methylene chloride then cooled to 0° and added was 110 μL, (0.75 mMol, distilled from calcium hydride) of triethylamine followed by 72 μL (0.62 mMol, Aldrich) of n-amylamine. The reaction mixture was stirred for 30 minutes then partitioned between 20 mL of ethyl acetate and 10 mL of 1M aqueous HCl solution. The organic layer was separated, dried (magnesium sulfate) and concentrated in vacuo to give a solid. The crude solid was purified by flash chromatography (Merck silica, 12×3.0 cm, 2:1 ethyl acetate/hexane) to give 171 mg (0.38 mMol, 72%) of title ester as a white solid.

B.
[1S-(1α,2α,3α,4α)]-2-[[3-[4-[(Pentylamino)thioxomethyl-2-oxazolyl]-7-oxabicyclo[2.2.1]hept-2-yl]methyl]benzenepropanoic acid, methyl ester Following the procedure of Example 1 Part P except substituting the Example 5 Part A amide for the Example 1 Part 0 amide, the title ester is obtained.

EXAMPLE 6

[1S-(1α,2α,3α,4α)]-2-[[3-4-[(Pentylamino)thioxomethyl]-2-oxazolyl]-7-oxabicyclo[2.2.1]hept-2-yl]methyl]benzenepropanoic acid Following the procedure of Example 2 except substituting the Example 5 ester for the Example 1 ester, the title acid is obtained.

EXAMPLE 7

[1S-(1α,2α,3α,4α)]-2-[[3-[4-[[(4-Cyclohexylbutyl)amino]thioxomethyl]-1H-imidazol-2-yl]-7-oxabicyclo[2.2.1]hept-2-yl]methyl]benzenepropanoic acid, methyl ester

A.
3-Amino-2-[[(1,1-dimethylethoxy)carbonyl]amino]-propanoic acid, benzyl ester To a stirred mixture of [bis(trifluoroacetoxy)iodosyl-benzene (2.00 g, 4.66 mmol) in 24 mL of 1:1 DMF-water was added N-α-Boc-asparagine benzyl ester (1.00 g, 3.11 mmol, preparation was described by Wang, G. et al, in J. Org. Chem., Vol, 42, p 1286–1290, 1977). This mixture was stirred in a cold water bath for 15 minutes at which time dry pyridine (0.50 mL, 6.21 mmol) was added. The mixture was stirred at room temperature for 4 hours and concentrated in vacuo. The crude product was partitioned between 10 mL of 1N HCl solution and ether (4×15 mL). The aqueous layer was neutralized with NaHCO$_3$, saturated with NaCl and extracted with EtOAc (4×15 mL). The combined EtOAc extracts were dried (MgSO$_4$), filtered and concentrated in vacuo to give 0.53 g (58%) of title amine.

TLC: silica gel, 6% CH$_3$OH/CH$_2$Cl$_2$, R$_f$ 0.44, Ce(SO$_4$)$_2$.

B.
[1S-[1α,2α,3α,4α]]-2-[[3-[[[2-[[(1,1-Dimethylethoxy)-carbonyl]amino]-3-oxo-3-(phenylmethoxy)propyl]amino]oxomethyl]7-oxabicyclo[2.2.1]hept-2-yl]methyl]benzenepropanoic acid, methyl ester To a stirred mixture of Example 2, Part E acid (3.75 g, 11.8 mmol), 1-hydroxybenzotriazole monohydrate (1.97 g, 11.8 mmol) and Part A amine (3.30 g, 11.8 mmol) in 80 mL of dry DMF under argon at 0° C. was added sequentially (C$_2$H$_5$)$_3$N (3.28 mL, 3.6 mmol) and ethyl-3-(3-dimethylamino)propyl carbodiimide hydrochloride salt (2.26 g, 11.8 mmol). The mixture was stirred at room temperature for 12 hours and concentrated in vacuo. The crude product was diluted with 400 mL of EtOAc and washed with 0.1N NaOH solution (3×40 mL), 1N HCl solution (2×40 mL), saturated NaHCO$_3$ solution (1×40 mL) and brine (1×80 mL). The EtOAc layer was dried (MgSO$_4$), filtered and concentrated in vacuo. This was chromatographed on Merck silica gel 60 using 2% CH$_3$OH/CH$_2$Cl$_2$ as eluant to give 1.87 g (27%) of title amide.

TLC: silica gel, 6% CH$_3$OH/CH$_2$Cl$_2$, R$_f$ 0.76, Ce(SO$_4$)$_2$.

C.
[1S-[1α,2α,3α,4α]]-2-[[3-[[[2-[[(1,1-Dimethylethoxy)-carbonyl]amino]-3-oxo-3-(phenylmethoxy)propyl]amino]thioxomethyl]-7-oxabicyclo[2.2.1]hept-2-yl]methyl]benzenepropanoic acid, methyl ester To a stirred mixture of Part B amide (650 mg, 1.12 mmol) in 14 mL benzene under argon was added Lawesson's reagent (2.93 g, 0.72 mmol). The mixture was heated at 65° C. under argon for 2 hours and cooled to room temperature. The mixture was diluted with 200 mL of ether and washed with saturated NaHCO$_3$ solution (1×30 mL) and brine (1×40 mL). The organic layer was dried (MgSO$_4$), filtered and concentrated in vacuo. Purification was effected by flash chromatography on 24 g of Merck silica gel 60 using 1:1 ether-hexane as eluant to give 350 mg (52%) of title thioamide.

TLC: silica gel, 3:1 ether-hexane, R$_f$ 0.58, Ce(SO$_4$)$_2$.

D.
[1S-[1α,2α,3α,4α]]-2-[[3-[1-[(1,1-Dimethylethoxy)carbonyl]-4,5-dihydro-5-[(phenylmethoxy)carbonyl]-1H-imidazol-2-yl]-7-oxabicyclo[2.2.1]hept-2-yl]methyl]benzenepropanoic acid, methyl ester To a stirred mixture of Part E thioamide (340 mg, 0.57 mmol), (C$_6$H$_5$)$_3$P (448 mg, 1.71 mmol) and (C$_2$H$_5$)$_3$N (0.24 mL, 1.71 mmol) in 6 mL of acetonitrile was added CCl$_4$ (0.62 mL, 6.27 mmol). The mixture was stirred at room temperature for 4 hours and diluted with 100 mL of ether and 10 mL of water. The resulting mixture was saturated with NaCl and extracted with ether (4×40 mL). The combined ether extracts were dried (MgSO$_4$), filtered and concentrated in vacuo. This was chromatographed on 20 g of Merck silica gel 60 using 200 mL of each of 2:1, 1:1, and 1:3 hexane-ether as eluant to give 180 mg (56%) of title Boc (or BOC)-imidazoline.

TLC: silica gel, ether, R$_f$ 0.24, Ce(SO$_4$)$_2$.

E.
[1S-[1α,2α,3α,4α]]-2-[[3-[5-[[(4-Cyclohexylbutyl)amino]carbonyl]-1-[(1,1-dimethylethoxy)carbonyl]-4,5-dihydro-1H-imidazol-2-yl]-7-oxabicyclo[2.2.1]hept-2-yl]methyl]benzenepropanoic acid, methyl ester To a stirred mixture of Part D Boc-imidazoline (180 mg, 0.32 mmol) in 10 mL of methanol under argon was added 20% Pd/C (36 mg, 20% based on the weight of Part D compound). The atmosphere was replaced with hydrogen by several vacuum-fill cycles. The mixture was stirred at room temperature for 4.5 hours and the catalyst was filtered off through a 4 μm polycarbonate film. The catalyst was rinsed with DMF (4×20 mL). The filtrate was concentrated in vacuo to give crude acid [1S-[1α,2α,3α,4α]]-2-[[3-[5-carboxy-1-[(1,1-dimethylethoxy)carbonyl]-4,5-dihydro-1H-imidazol-2-yl]-7-oxabicyclo[2.2.1]hept-2yl]methyl]benzenepropanoic acid, methyl ester. To a stirred mixture of this acid, 1-hydroxybenzotriazole monohydrate (54 mg, 0.32 mmol) and 4-cyclohexylbutyl amine hydrochloride salt (74 mg, 0.38 mmol) in 3 mL of DMF under argon at 0° C. was added sequentially (C$_2$H$_5$)$_3$N (0.11 mL, 0.79 mmol) and ethyl-3-(3-dimethylamino)propyl carbodiimide hydrochloride salt (61 mg, 0.32 mmol). The mixture was stirred at room temperature for 18 hours and concentrated in vacuo. The crude product was partitioned between 150 mL of EtOAc and 0.1 N NaOH solution (2×25 mL), 1N HCl solution (2×25 mL) and saturated NaHCO$_3$ solution (1×25 mL). The organic layer was dried (MgSO$_4$), filtered and concentrated in vacuo. This was chromatographed on 10 g of Merck silica gel 60 using 2% CH$_3$OH/CH$_2$Cl$_2$ as eluant to give 42.1 mg (22%) of title amide.

TLC: silica gel, 6% CH$_3$OH/CH$_2$Cl$_2$, R$_f$ 0.58, Ce(-SO$_4$)$_2$.

F.

[1S-(1α,2α,3α,4α)]-2-[[3-[4-[[(4-Cyclohexylbutyl)amino]carbonyl]-1H-imidazol-2-yl]-7-oxabicyclo[2.2.1]hept-2-yl]methyl]benzenepropanoic acid, methyl ester To a stirred mixture of Part E amide (555 mg, 0.94 mmol) in 3 mL of dry CH$_2$Cl$_2$ at 0° C. was added 6 mL of trifluoroacetic acid (TFA). The mixture was stirred at room temperature for 3 hours. The mixture was diluted with 40 mL of toluene and concentrated in vacuo to give [1S-[1α,2α,3α,4α]]-2-[[3-[5-[[(4-cyclohexylbutyl)amino]carbonyl]-4,5-dihydro-1H-imidazol-2-yl]-7-oxabicyclo[2.2.1]hept-2-yl]methyl]benzenepropanoic acid, methyl ester. The crude imidazole-TFA salt was diluted with 150 mL of EtOAc and washed once with 40 mL of saturated NaHCO$_3$ solution. The aqueous layer was extracted with EtOAc (1×100 mL). The combined EtOAc extracts were dried (MgSO$_4$), filtered and concentrated in vacuo. To this crude imidazoline in 15 mL of CHCl$_3$ was added MnO$_2$ (570 mg, 6.55 mmol). The mixture was stirred at room temperature for 64 hours at which time MnO$_2$ (570 mg, 6.55 mmol) was added. The mixture was stirred at room temperature for 1 day and another amount of MnO$_2$ (290 mg, 3.28 mmol) was added. The mixture was stirred at room temperature for one more day and again MnO$_2$ (190 mg, 2.18 mmol) was added. The mixture was stirred at room temperature for 1 day and MnO$_2$ was filtered off through a pad of Celite and the pad was rinsed with CHCl$_3$ (6×30 mL). The filtrate was concentrated in vacuo and chromatographed on 40 g of Merck silica gel 60 (the silica gel was pretreated with 0.1% Et$_3$N in CH$_2$Cl$_2$ and then washed with CH$_2$Cl$_2$) using 150 mL of CH$_2$Cl$_2$ and 150 mL of 2% CH$_3$OH/CH$_2$Cl$_2$ as eluant to give 370 mg (76%) of imidazole.

TLC: silica gel, 6% CH$_3$OH/CH$_2$Cl$_2$, R$_f$ 0.66, Ce(-SO$_4$)$_2$.

G.

[1S-(1α,2α,3α,4α)]-2-[[3-[4-[[(4-Cyclohexylbutyl)amino]thioxomethyl]-1H-imidazol-2-yl]-7-oxabicyclo[2.2.1]hept-2-yl]methyl]benzenepropanoic acid, methyl ester Following the procedure of Example 1 Part P except substituting the Example 7 Part F amide for the Example 1 Part O amide the title ester is obtained.

EXAMPLE 8

[1S-(1α,2α,3α,4α)]-2-[[3-[4-[[(4-Cyclohexylbutyl)amino]thioxomethyl]-1H-imidazol-2-yl]-7-oxabicyclo[2.2.1]hept-2-yl]methyl]benzenepropanoic acid Following the procedure of Example 2 except substituting the Example 7 amide for the Example 1 amide, the title acid is obtained.

EXAMPLE 9

[1S-(1α,2α,3α,4α)]-2-[[3-[4-[[[2-(4-Chlorophenyl)ethyl]amino]thioxomethyl]-2-oxazolyl]-7-oxabicyclo[2.2.1]hept-2-yl]methyl]benzenepropanoic acid

A.

[1S-(1α,2α,3α,4α)]-2-[[3-[4-[[[2-(4-Chlorophenyl)ethyl]amino]carbonyl]-2-oxazolyl]-7-oxabicyclo[2.2.1]hept-2-yl]methyl]benzenepropanoic acid, methyl ester To a solution of 150 mg (0.39 mmol) of oxazole acid prepared in Example 3, Part J in 3 mL of dry methylene chloride (distilled from phosphorous pentoxide) was added at room temperature a small drop of DMF then 45 μL (0.51 mmol, Aldrich) of oxalyl chloride. The solution was stirred until gas evolution ceased, about 30 minutes, then concentrated in vacuo to give the acid chloride as a pale yellow solid.

To a solution of the crude acid chloride (about 0.39 mmol) in 3 mL of dry methylene chloride cooled in an ice-bath was added 82 μL (0.58 mmol, distilled from calcium hydride) of triethylamine followed by 66 μL (0.47 mmol, Aldrich) of 2-(4-chlorophenyl)ethylamine. The reaction mixture was stirred for 15 minutes then partitioned between 20 mL of 1M aqueous HCl solution and 20 mL of ethyl acetate. The organic layer was separated, dried (magnesium sulfate) and concentrated in vacuo to give a solid. The crude material was recrystallized (ethyl acetate/hexane) to afford 163 mg (0.31 mmol, 80%) of title ester as white needles, mp 188°–189° C.

B.

[1S-(1α,2α,3α,4α)]-2-[[3-[4-[[[2-(4-Chlorophenyl)ethyl]amino]thioxomethyl]-2-oxazolyl]-7-oxabicyclo[2.2.1]hept-2-yl]methyl]benzenepropanoic acid, methyl ester Following the procedure of Example 1 Part P except substituting the Example 9 Part A amide for the Example 1 Part O amide, the title ester is obtained.

EXAMPLE 10

[1S-(1α,2α,3α,4α)]-2-[[3-[4-[[[2-(4-Chlorophenyl)ethyl]amino]thioxomethyl]-2-oxazolyl]-7-oxabicyclo[2.2.1hept-2-yl]methyl]benzenepropanoic acid Following the procedure of Example 2 except substituting the Example 9 ester for the Example 1 ester, the title acid is obtained.

EXAMPLE 11

[1S-[1α2α(Z),3α,4α]]-6-[3-[4-[[(4-Cyclohexylbutyl)amino]thioxomethyl]-2-oxazolyl]-7-oxabicyclo[2.2.1]hept-2-yl]-4-hexenoic acid

A.

[(1,1-Dimethylethoxy)carbonyl]-N-(4-cyclohexylbutyl)-L-serinamide

To a solution of 575 mg of 4-cyclohexylbutyl amine hydrochloride (3.0 mmol), 615 mg t-butyloxy carbonyl-L-serine (3.0 mmol, 1.0 equiv), 405 mg 1-hydroxybenzotriazole hydrate (3.0 mmol, 1.0 equiv), and 387 mg diisopropylethylamine (3.0 mmol, 1.0 equiv) in 10 mL dry tetrahydrofuran (THF) stirring under argon at 0°, was added 618 mg 1,3-dicyclohexylcarbodiimide (3.0 mmol, 1.0 equiv) in a single portion. A precipitate slowly formed. After 1 hour the mixture was warmed to room temperature and stirred for 4 hours. After dilution with ethyl acetate, the mixture was filtered, and the filtrate was washed with a pH 1 salt solution (formed by mixing water, brine, and 1 M aqueous HCl solution). Further washing (twice) with 1 M NaHCO$_3$ was followed by drying over Na$_2$SO$_4$ and evaporation to give 1.1 g of crude title amide.

TLC (10% [10% conc. aqueous NH$_3$ in CH$_3$OH] in CH$_2$Cl$_2$—anisaldehyde):

| cyclohexylbutylamine HCl | 0.27 |
|---|---|
| title amide | 0.47 |

B. N-(4-Cyclohexylbutyl)-L-serinamide

To a solution of 1.1 g crude Part A amide in 4 mL CH$_2$Cl$_2$ at room temperature was added 4 mL trifluoroacetic acid. The mixture was stirred for hours. After solvent evaporation, residual trifluoroacetic acid was azeotropically removed by rotoevaporation with CHCl$_3$. Flash chromatography (150 g silica, 10% [10% concentrated aqueous NH$_3$ in CH$_3$OH] in CH$_2$Cl$_2$) gave, after azeotroping with toluene and exposure to high vacuum, 495 mg of pure title amine as a white solid. The yield of title amine was 68% overall from 4-cyclohexylbutyl amine hydrochloride.

TLC (10% [10% conc. aqueous NH$_3$ in CH$_3$OH] in CH$_2$Cl$_2$—anisaldehyde):

| Part A amide | 0.47 |
|---|---|
| title amine | 0.17 |

$^{13}$C NMR (67.8 MHz in CDCl$_3$): 173.4, 64.6, 56.3, 39.1, 37.3, 36.9, 33.1, 29.6, 26.5, 26.2, 24.0

C.
[1S-[1α,2α(Z),3α,4α]]-6-[3-(Hydroxymethyl)-7-oxabicyclo[2.2.1]hept-2-yl]-4-hexenoic acid, methyl ester To a partial solution of 36.27 g of [4aR-(4aα,5β,8β,-8aβ)]-octahydro-5,8-epoxy-1H-2-benzopyran-3-ol (prepared as described in U.S. Pat. No. 4,143,054) (0.23 mol) and 3-carboxypropyltriphenylphosphonium bromide (127.34 g, 0.37 mol) in 600 mL of dry THF under argon at 3° C. was added dropwise over 1 hour a solution of 370.6 mL of potassium t-amylate (0.68 mol of a 1.8M toluene solution) with mechanical stirring. Initially the reaction temperature reached a maximum of 8° C. and subsequently leveled off to 4° C. for the remainder of the base addition. The reaction was then run at room temperature for 90 minutes. A 0° C. ice bath was introduced and the reaction was quenched by the addition of 152 mL of glacial acetic acid, over 30 minutes. Solvents were removed in vacuo (azeotroped with toluene). Water (640 mL) and 50 mL of concentrated HCl were added (pH 2.6). Dilution with 640 mL of ethyl acetate, the addition of 149 g of NaCl and a few seed crystals of 3-carboxypropyltriphenylphosphonium bromide was followed by vigorous stirring for 15 minutes. The precipitate was collected by filtration and washed with 2 portions each of 320 mL of ethyl acetate. The ethyl acetate layer was separated, the aqueous layer was extracted with ethyl acetate (2×200 mL each), the combined ethyl acetate layers were dried over MgSO$_4$ and concentrated. Aqueous 5% K$_2$CO$_3$ was added (507 mL) followed by vigorous stirring for 1 hour. No precipitation occurred. The reaction mixture was concentrated to a paste and suspended in 508 mL of water. Several hours of vigorous stirring produced no precipitate. The water was decanted off and the residue was suspended in 200 mL of aqueous 5% K$_2$CO$_3$ solution. After vigorous stirring, a light tan solid was collected by filtration and rinsed several times with water. The combined aqueous layers were extracted 5× with 1:1 toluene/ether (230 mL each). After cooling the combined aqueous layers with a 0° C. ice bath, concentrated HCl was added to pH 2.5, followed by extraction 1× with 460 mL then 2× with 230 mL each of ethyl acetate. The combined ethyl acetate layers were dried over MgSO$_4$ and evaporated in vacuo to yield 49.74 of an amber oil. Trituration from 330 mL of ether (room temperature, overnight) oiled out phosphorous by-products. The ether solution was decanted away from the dark red oil into a separatory funnel, and the oil which was carried over by the decantation was drained off (1.56 g). Evaporation of the ether solution in vacuo yielded 43.08 g of [1S-[1α,2α(Z),3α,4α]]-6-[3-hydroxymethyl)-7-oxabicyclo[2.2.1]hept-2-yl]-4-hexenoic acid in the form of a viscous yellow oil.

$^1$H NMR indicated a product: triphenylphosphine oxide: ether molar ratio of 23:1:1.8 (mass % 93:4.7:2.2). Yield exclusive of triphenylphosphine oxide/ether, 40.06 g (72.5%).

Acetyl chloride (5.20 mL, 0.073 mol) was added dropwise to 80 mL of methanol at room temperature under argon. The acetyl chloride/methanol solution was then added to a solution of 42.98 g (0.18 mol) in 700 mL of methanol in one portion. Stirring was continued for 3 hours. Triethylamine was added (0.09 mol, 12.21 mL), methanol was removed in vacuo, and the residue was partitioned between 300 mL of ethyl acetate and 150 mL of water. After separation of the layers, the aqueous layer was extracted with 150 mL of ethyl acetate, the combined ethyl acetate layers were washed with brine, dried over Na$_2$SO$_4$ and evaporated in vacuo to yield 43.06 g of a viscous tan oil. Flash chromatography on 1350 g of E. Merck Kieselgel 60 silica gel (240–400 mesh, 75/25 ether/hexanes, then ether after the desired product began eluting off the column) yielded 35.74 g title ester in the form of a viscous light yellow oil, free from triphenylphosphine oxide by NMR.

$^1$H NMR (CDCl$_3$, ref. TMS): δ5.41–5.38, m (2H); 4.49, d, J=4.69Hz (1H); 4.22, d, J=4.69Hz (1H); 3.73–3.69, m (1H); 3.67, s, (3H); 3.60, m (1H); 2.37, br s (4H); 2.12–1.99, m (3H); 1.97–1.85, m (1H); 1.72, m (2H); 1.46, m (2H).

$^{13}$C NMR (CDCl$_3$, ref. 77.00): δ173.50, 130.42, 28.63, 80.23, 79.22, 61.74, 51.49, 48.95, 46.45, 3.86, 29.69, 29.31, 25.94, 22.92

D.
[1S-[1α,2α(Z),3α,4α]]-6-[3-(Carboxy)-7-oxabicyclo[2.2.1]hept-2-yl]-4-hexenoic acid, methyl ester To a solution of 2.43 g of impure Part C alcohol (80% pure=1.94 g, 7.6 mmol, contaminated with triphenylphosphine oxide) in 40 mL acetone under argon at 0°, was added slowly 8 mL Jones' Reagent (2.6 M in Cr$^{VI}$). The red color of the reagent persisted toward the end of the addition. This resulting precipitated mixture was stirred for 20 minutes before 2-propanol was added to quench excess reagent. Still at 0°, 3M aqueous NaHSO$_3$ solution was added with stirring until all salts dissolved. Brine was added, and extraction (3 times) with ethyl acetate followed. After drying the extracts over Na$_2$SO$_4$ and solvent evaporation, flash chromatography (150 g silica, 25% to 40% [5% acetic acid in ethyl acetate] in hexane gradient) afforded, after azeotropic removal of acetic acid with toluene, 1.91 g of an oil. This oil was impure title acid (80% pure=1.53 g, contaminated with triphenylphosphine oxide), obtained in 75% yield.

TLC (50% [5% acetic acid in ethyl acetate] in hexane—anisaldehyde):

| Part C alcohol | 0.33 |
|---|---|
| title acid | 0.35 |

$^{13}$C NMR (67.8 MHz in CDCl$_3$): 175.3, 173.1, 129.1, 128.8, 78.0, 78.0, 51.6, 1.1, 47.4, 33.5, 28.8, 28.5, 26.9, 22.5

E.
[1S-[1α,2α(Z),3α(R*),4α]]-6-[3-[[[2-[(4-Cyclohexylbutyl)amino]-1-(hydroxymethyl)-2-oxoethyl]amino]-carbonyl-7-oxabicyclo[2.2.1]hept-2-yl]-4-hexenoic acid, methyl ester To a solution of 733 mg impure Part D acid (80% pure=586 mg, 2.2 mmol, 1.1 equiv, contaminated with triphenylphosphine oxide) in 4 mL dry tetrahydrofuran (THF) under argon was added 356 mg 1,1'-carbonyldiimidazole (2.2 mmol, 1.1 equiv), and the mixture was left for 1 hour. Since a large volume of precipitate had formed, 5 mL dry THF was added, and the mixture was gently warmed to obtain a solution. (TLC showed a stable acylimidazole.) After stirring 30 minutes, a solution of 495 mg Part B amine (2.0 mmol) in 10 mL dry THF was added using an additional 5 mL THF to quantitatively transfer the amine. TLC of the homogeneous mixture after 1 hour stirring at room temperature indicated very slow reaction. Therefore, THF was evaporated by passing argon over the mixture overnight until its volume was reduced to 2 mL and a precipitate had formed. Addition of 5 mL THF redissolved all precipitate. After 5 hours more stirring, the mixture was evaporated, and flash chromatography (150 g silica, 50% to 100% ethyl acetate in hexane gradient, then 0% to 10% CH$_3$OH in ethyl acetate gradient) gave 230 mg of pure title hydroxybisamide as an oil. The yield of title hydroxybisamide was 23%.

Also isolated were the isomeric aminoesteramide (27%) and the 2:1 adduct (16%). These byproducts could be converted in good yields to title hydroxybisamide by transesterification with KCN in CH$_3$OH at room temperature, although the aminoesteramide may isomerize spontaneously.

TLC (50% [5% acetic acid in ethyl acetate] in hexane—anisaldehyde):

| Part B amine | 0.00 |
|---|---|
| Part D acid | 0.38 |
| acylimidazole | 0.18 |
| title hydroxybisamide | 0.22 |
| aminoesteramide | 0.04 |
| 2:1 adduct | 0.33 |

$^{13}$C NMR (67.8 MHz in CDCl$_3$): 173.3, 172.8, 170.4, 129.2, 129.0, 78.9, 78.8, 62.7, 54.0, 53.8, 51.3, 47.9, 39.4, 37.3, 36.9, 33.6, 33.1, 29.5, 29.4, 28.6, 27.2, 26.4, 26.1, 24.0, 22.6

F.
[1S-[1α,2α(Z),3α(R*),4α]]-6-[3-[4-[[(4-Cyclohexylbutyl)amino]carbonyl]-4,5-dihydro-2-oxazolyl]-7-oxabicyclo[2.2.1]hept-2-yl]4-hexenoic acid, methyl ester This chemistry is described by M. J. Miller, P. G. Mattingly, M. A. Morrison, and J. F. Kerwin, Jr., *J. Am. Chem. Soc.*, 1980, 102, 7026.

To a solution of 240 mg of pure Part E hydroxybisamide (0.48 mmol) in 3 mL dry THF under argon at room temperature, was added 189 mg triphenylphosphine (0.72 mmol, 1.5 equiv), 73 mg triethylamine (0.72 mmol, 1.5 equiv), and 89 mg CCl$_4$ (0.58 mmol, 1.2 equiv), and the mixture was heated to reflux. After 1 hour another aliquot each of CCl$_4$ and triethylamine were added, and after 2.5 hours more another aliquot of each were added again. 2 hours later another aliquot each of CCl$_4$ and triethylamine and half an aliquot (95 mg) of triphenylphosphine were added. After 2 hours more, TLC finally indicated complete consumption of Part E hydroxybisamide, and the initially colorless, homogeneous mixture had formed a white precipitate and had darkened. Solvent evaporation was followed by flash chromatography (silica, 15% acetone in toluene) which afforded 190 mg of pure title oxazoline, an oil. The oxazoline was obtained in 83% yield.

TLC (20% acetone in toluene—anisaldehyde):

| Part E hydroxybisamide | 0.07 |
|---|---|
| title oxazoline | 0.29 |

$^{13}$C NMR (67.8 MHz in CDCl$_3$): 173.1, 171.2, 169.1, 129.3, 128.9, 79.0, 78.9, 69.6, 68.3, 51.3, 48.2, 46.3, 39.0, 37.4, 36.9, 33.7, 33.1, 29.6, 29.5, 28.7, 27.1, 26.5, 26.2, 24.0, 22.7

G.
[1S-[1α,2α(Z),3α,4α]]-6-[3-[4-[[(4-Cyclohexylbutyl)amino]carbonyl]-2-oxazolyl]-7-oxabicyclo[2.2.1]hept-2-yl]-4-hexenoic acid, methyl ester This chemistry is described by D. L. Evans, D. K. Minster, U. Jordis, S. M. Hecht, A. L. Mazzu, Jr., and A. I. Meyers, *J. Org. Chem.*, 1979, 44, 497.

To a solution of 190 mg of pure Part F oxazoline (0.40 mmol) in 10 mL CHCl$_3$, was added 200 mg untitrated NiO$_2$, and the heterogenous mixture was stirred at room temperature. TLC indicated some progress in the first 1 hour, but then reaction stopped. Over 1 day, five additional aliquots of the reagent were added until the reaction was complete. The mixture was diluted with ethyl acetate, and this was stirred with 3M aqueous NaHSO$_3$ solution until the black color of the NiO$_2$ disappeared and most of the solids dissolved. Extraction (3 times) with ethyl acetate was followed by drying over Na$_2$SO$_4$ and evaporation. Flash chromatography (silica, 25% to 35% ethyl acetate in hexane gradient) afforded 90 mg of pure title oxazole, a solid. The oxazole was obtained in 48% yield.

TLC (100% ethyl acetate—anisaldehyde):

| Part F oxazoline | 0.52 |
|---|---|
| title oxazole | 0.81 |

$^{13}$C NMR (67.8 MHz in CDCl$_3$): 173.2, 163.8, 160.5, 140.4, 136.0, 129.4, 128.5, 79.5, 79.3, 51.4, 49.6, 46.6, 39.0, 37.4, 37.0, 33.7, 33.3, 29.8, 29.7, 28.9, 27.8, 26.6, 26.3, 24.1, 22.7

H.
[1S-[1α,2α(Z),3α,4α]]-6-[3-[4-[[(4-Cyclohexylbutyl)amino]thioxomethyl]-2-oxazolyl]-7-oxabicyclo[2.2.1-]hept-2-yl]-4-hexenoic acid, methyl ester Following the procedure of Example 1 Part P except substituting the Example 11 Part G amide for the Example 1 Part O amide, the title compound is obtained.

EXAMPLE 12

[1S-[1α,2α(Z),3α,4α]]-6-[3-[4-[[(4-Cyclohexylbutyl)amino]thioxomethyl]-2-oxazolyl]-7-oxabicyclo[2.2.1-]hept-2-yl]-4-hexenoic acid Following the procedure of Example 2 except substituting the Example 11 ester for the Example 1 ester, the title acid is obtained.

Examples of additional compounds in accordance with the present invention which may be prepared following the procedures outlined in the specification and working Examples include, but are not limited to, the following.

| Example No. | $(CH_2)_m$ m | $(CH_2)_n$ n | X | Y(position) | $R^1$ | $R^2$ | R |
|---|---|---|---|---|---|---|---|
| 13 | 1 | 2 | O | -(2) | —$C_6H_{13}$ | $CH_3$ | $CO_2H$ |
| 14 | 2 | 2 | O | -(2) | —$(CH_2)_4$-cyclohexyl(S) | $CH_3$ | $CO_2H$ |
| 15 | 2 | 1 | NH | -(3) | cyclopentyl(S) | H | $CONHSO_2CH_3$ |
| 16 | 1 | 2 | S | -(4) | —$C_2H_4$-C$_6$H$_4$-Cl | H | —$CH_2$-5-tetrazolyl |
| 17 | 2 | 3 | O | -(2) | $C_6H_5$ | $C_6H_5$ | $CO_2H$ |
| 18 | 1 | 2 | NH | -(3) | —$CH_2C_6H_5$ | H | —$CH_2$-5-tetrazolyl |
| 19 | 1 | 2 | O | -(2) | i-$C_3H_7$ | H | $CONHSO_2C_6H_5$ |
| 20 | 1 | 3 | O | -(2) | —$CH_2$-cyclohexyl(S) | n-$C_4H_9$ | $CONHSO_2CH_2C_6H_5$ |
| 21 | 1 | 2 | NH | -(3) | —$(CH_2)_3$-cyclopropyl | H | $CO_2H$ |
| 22 | 2 | 2 | O | -(3) | cyclobutyl | $CH_2C_6H_5$ | $CO_2CH_3$ |
| 23 | 1 | 2 | S | -(3) | $C_2H_5$ | H | $CO_2Li$ |
| 24 | 1 | 2 | O | -(2) | —C$_6$H$_4$-Cl | H | $CO_2C_2H_5$ |
| 25 | 1 | 2 | O | -(2) | $(CH_2)_2C_6H_5$ | $CH_3$ | $CO_2H$ |
| 26 | 1 | 3 | O | -(4) | n-$C_3H_7$ | $CH_2C_6H_5$ | —$CH_2$-5-tetrazolyl |
| 27 | 1 | 2 | NH | -(3) | n-$C_5H_{11}$ | H | $CO_2H$ |

-continued

| | | | | | | | |
|---|---|---|---|---|---|---|---|
| 28 | 2 | 3 | O | -(2) | [cyclohexyl-S] | CH$_3$ | CONHC$_6$H$_5$ |
| 29 | 1 | 2 | O | -(2) | —(CH$_2$)$_6$— | | CONH$_2$ |
| 30 | 2 | 0 | O | -(3) | n-C$_4$H$_9$ | n-C$_4$H$_9$ | CO$_2$H |
| 31 | 1 | 0 | NH | -(2) | C$_6$H$_5$ | H | CONHCH$_3$ |
| 32 | 1 | 2 | O | -(2) | —(CH$_2$)$_4$—imidazolyl | H | CO$_2$H |
| 33 | 2 | 2 | O | -(3) | —(CH$_2$)$_5$-pyridyl | H | CO$_2$H |
| 34 | 1 | 1 | NH | -(2) | —(CH$_2$)$_6$—N-pyrrolidinyl | H | CONHCH$_2$C$_6$H$_5$ |
| 35 | 1 | 2 | O | -(2) | —(CH$_2$)$_4$-tetrahydropyranyl | H | CO$_2$H |

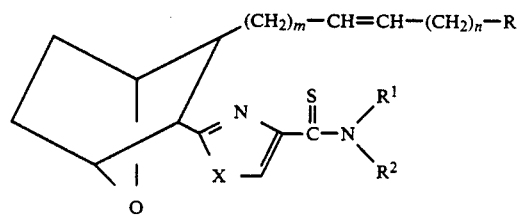

| Example No. | (CH$_2$)$_m$ m | (CH$_2$)$_n$ n | X | R$^1$ | R$^2$ | R |
|---|---|---|---|---|---|---|
| 36 | 1 | 2 | O | C$_6$H$_{13}$ | CH$_3$ | CO$_2$H |
| 37 | 2 | 2 | O | —(CH$_2$)$_2$-[cyclohexyl-S] | C$_2$H$_5$ | CO$_2$H |
| 38 | 3 | 1 | NH | [cyclopentyl-S] | i-C$_3$H$_7$ | CONHSO$_2$CH$_3$ |
| 39 | 1 | 2 | S | —C$_2$H$_4$—C$_6$H$_4$—Cl | H | CH$_2$-5-tetrazolyl |
| 40 | 2 | 3 | O | C$_6$H$_5$ | C$_6$H$_5$ | CO$_2$H |
| 41 | 1 | 2 | NH | —CH$_2$C$_6$H$_5$ | CH$_2$C$_6$H$_5$ | CONHC$_6$H$_5$ |
| 42 | 1 | 2 | O | i-C$_3$H$_7$ | H | CONHSO$_2$C$_6$H$_5$ |
| 43 | 1 | 3 | O | —CH$_2$-[cyclohexyl-S] | n-C$_4$H$_9$ | CONHSO$_2$CH$_2$C$_6$H$_5$ |
| 44 | 1 | 2 | NH | —(CH$_2$)$_3$-cyclopropyl | H | CONHCH$_2$C$_6$H$_5$ |

-continued

| # | m | n | Z | | R¹ | R |
|---|---|---|---|---|---|---|
| 45 | 2 | 2 | O | 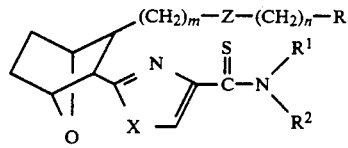 | $CH_2C_6H_5$ | $CO_2CH_3$ |
| 46 | 1 | 2 | S | $C_2H_5$ | H | $CO_2Li$ |
| 47 | 1 | 3 | NH | 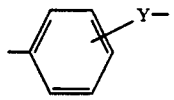-Cl | $C_2H_5$ | $CO_2C_2H_5$ |
| 48 | 1 | 2 | O | $-(CH_2)_2C_6H_5$ | $CH_3$ | $CO_2H$ |
| 49 | 1 | 3 | O | $n-C_3H_7$ | $CH_2C_6H_5$ | $CH_2$-5-tetrazolyl |
| 50 | 1 | 2 | NH | $n-C_5H_{11}$ | H | $CO_2H$ |
| 51 | 2 | 3 | O | 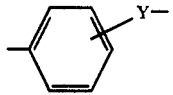 | $CH_3$ | $CONHCH_3$ |
| 52 | 1 | 2 | O | $-(CH_2)_6-$ | | $CONH_2$ |

What is claimed is:

1. A compound having the formula

including all stereoisomers thereof, wherein
m is 1, 2 or 3;
n is 0, 1, 2, 3 or 4;
Z is

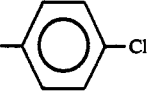

wherein Y is O, a single bond or vinyl (—CH═CH—), with the provisos that when n is 0, if Z is

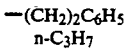

then Y cannot be O; and when Y=vinyl, n=0;
R is $CO_2H$, $CO_2$alkali metal, $CO_2$lower alkyl, $CH_2OH$, $CONHSO_2R^3$, $CONHR^{3a}$ or $-CH_2$-5-tetrazolyl, with the proviso that when R is $-CH_2$-5-tetrazolyl, and Z is other than $-(CH_2)_2-$, n is 1, 2, 3 or 4;
X is O, S is NH;
$R^1$ is hydrogen, lower alkyl, lower alkenyl, lower alkynyl, aryl, aralkyl, cycloalkyl, cycloalkylalkyl, cycloheteroalkyl, cycloheteroalkylalkyl, heteroaryl or heteroarylalkyl, each of $R^1$ being unsubstituted or optionally substituted with a lower alkyl, aryl, cycloalkyl or cycloalkylalkyl group;
$R^2$ is hydrogen, lower alkyl, aryl, or aralkyl, or $R^1$ and $R^2$ together with the N to which they are linked form a 5- to 8-membered ring which contains only the single N heteroatom; and
$R^3$ is lower alkyl, aryl or aralkyl; and
$R^{3a}$ is hydrogen, lower alkyl, aryl or aralkyl, wherein
the term "aryl" by itself or as part of another group refers to a monocyclic or bicyclic aromatic group containing from 6 to 10 carbons in the ring portions, which is unsubstituted or substituted with 1 or 2 substituents which are lower alkyl, trifluoromethyl, halogen, lower alkoxy, arylalkoxy, hydroxy, alkylthio, alkylsulfinyl, alkylsulfonyl, arylthio, arylsulfinyl and/or arylsulfonyl;

the term "cycloalkyl" by itself or as part of another group refers to a saturated cyclic hydrocarbon group containing 3 to 12 carbons, which is unsubstituted or substituted with halogen, lower alkyl, alkoxy and/or hydroxy;

the term "cycloheteroalkyl" by itself or as part of another group refers to a 5-, 6- or 7-membered saturated ring which includes 1 or 2 heteroatoms which are nitrogen, oxygen and/or sulfur;

the term "heteroaryl" by itself or as part of another group refers to 5- or 6-membered aromatic ring which includes 1 or 2 heteroatoms which are nitrogen, oxygen or sulfur;

the term "lower alkyl" or "alkyl" by itself or as part of another group refers to a straight or branched chain radical of up to 18 carbons which is unsubstituted or substituted with 1, 2 or 3 halogen, aryl, alkyl-aryl, haloaryl, cycloalkyl, alkylcycloalkyl, hydroxy or carboxy substituents;

The term "lower alkenyl" or "alkenyl" by itself or as part of another group refers to a carbon chain of up to 16 carbons containing one double bond and which is unsubstituted or substituted with a halogen substituent; and the term "lower alkynyl" or "alkynyl" by itself or as part of another group refers to a carbon chain of up to 16 carbons containing one triple bond.

2. The compound as defined in claim 1 having the formula

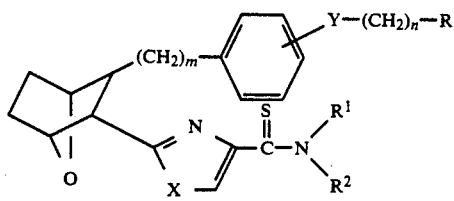

3. The compound as defined in claim 2 having the formula

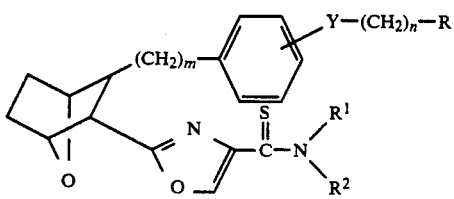

4. The compound as defined in claim 2 where m=1 and n=2.

5. The compound as defined in claim 2 having the formula

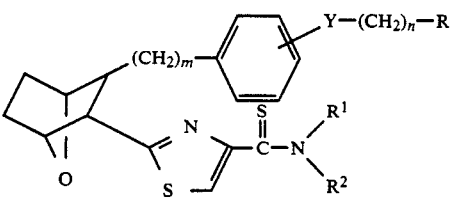

6. The compound as defined in claim 2 having the formula

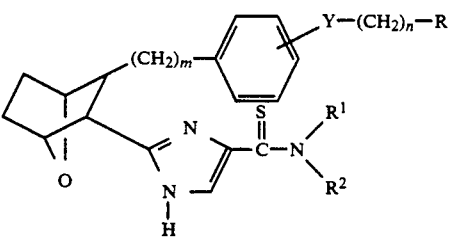

7. The compound as defined in claim 2 wherein R is $CO_2H$, $CONHSO_2R^3$ or —$CH_2$-5-tetrazolyl.

8. The compound as defined in claim 3 having the formula

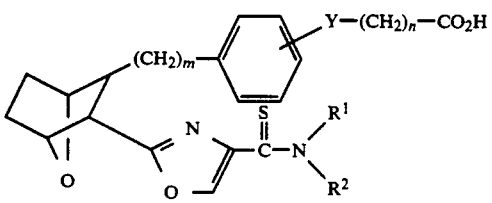

9. The compound as defined in claim 1 wherein Z is

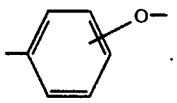

10. The compound as defined in claim 1 wherein Z is

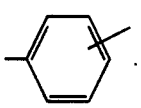

11. The compound as defined in claim 1 wherein Z is

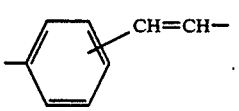

12. The compound as defined in claim 1 wherein Z is —$(CH_2)_2$— or —CH=CH—.

13. The compound as defined in claim 2 having the name [1S-(1α,2α,3α,4α)]-2-[[3-[4-[[(4-cyclohexylbutyl)amino]thioxomethyl]-2-oxazolyl]-7-oxabicyclo[2.2.1]hept-2-yl]methyl]benzenepropanoicacid, or esters or salts thereof.

14. A method of inhibiting platelet aggregation and bronchoconstriction, which comprises administering to the circulatory system of a mammalian host an effective amount of a compound as defined in claim 1.

15. The method as defined in claim 14 wherein said compound is administered in an amount within the range of from about 0.1 to about 100 mg/kg.

16. A composition for inhibiting platelet aggregation and bronchoconstriction comprising an effective amount of a compound as defined in claim 1, and a pharmaceutically acceptable carrier therefor.

17. A method of inhibiting platelet aggregation which comprises administering to a mammalian host an effective amount of a compound as defined in claim 1.

18. A method of inhibiting bronchoconstriction associated with asthma, which comprises administering to a mammalian host an effective amount of a compound as defined in claim 1.

19. A method for improving post-ischemic myocardial function, which comprises administering to a mammalian host in need of such treatment an effective amount of a compound as defined in claim 1.

20. A method for treating toxemia during pregnancy, which comprises administering to a mammalian host in need of such treatment an effective amount of a compound as defined in claim 1.

21. A method for preventing or reducing venous thrombosis, which comprises administering to a mammalian host in need of such treatment an effective amount of a compound as defined in claim 1.

22. A method for preventing or reducing platelet loss during extracorporeal circulation, which comprises administering to a mammalian host in need of such treatment an effective amount of a compound as defined in claim 1.

23. A method for treating burn injuries and/or promoting wound healing, which comprises administering to a mammalian host in need of such treatment an effective amount of a compound as defined in claim 1 in systemic or topical form.

24. A method for reducing post-ischemic myocardial injury, which comprises administering to a mammalian host in need of such treatment an effective amount of a compound as defined in claim 1 and an effective amount of a thrombolytic agent within 6 hours of a myocardial infarction.

25. The method as defined in claim 24 wherein said thrombolytic is t-PA, streptokinase, urokinase, prourokinase or anisoylated plasminogen-streptokinase activator complex.

* * * * *